(12) United States Patent
Kobayashi et al.

(10) Patent No.: US 8,557,572 B2
(45) Date of Patent: Oct. 15, 2013

(54) CULTURE APPARATUS

(75) Inventors: Kuniyoshi Kobayashi, Oizumi-machi (JP); Hiroki Busujima, Ota (JP); Yasuhiro Kikuchi, Ota (JP); Yuichi Tamaoki, Oizumi-machi (JP); Shinji Sugimoto, Ota (JP); Tetsuo Sakurai, Ota (JP)

(73) Assignee: Panasonic Healthcare Co., Ltd., Ehime (JP)

( * ) Notice: Subject to any disclaimer, the term of this patent is extended or adjusted under 35 U.S.C. 154(b) by 0 days.

(21) Appl. No.: 13/527,054

(22) Filed: Jun. 19, 2012

(65) Prior Publication Data
US 2012/0258528 A1 Oct. 11, 2012

Related U.S. Application Data

(63) Continuation of application No. 12/707,122, filed on Feb. 17, 2010, now Pat. No. 8,216,830, which is a continuation of application No. PCT/JP2009/064595, filed on Aug. 20, 2009.

(30) Foreign Application Priority Data

Aug. 27, 2008 (JP) ................................. 2008-218615

(51) Int. Cl.
*C12M 1/36* (2006.01)
*C12M 1/12* (2006.01)
(52) U.S. Cl.
USPC ........................................ 435/303.1; 435/809
(58) Field of Classification Search
USPC ........... 435/303.1, 809; 422/298, 305, 27, 29, 422/33
See application file for complete search history.

(56) References Cited

U.S. PATENT DOCUMENTS 3,987,133 A * 10/1976 Andra ........................... 261/130
4,131,011 A 12/1978 Ling
4,336,329 A 6/1982 Hesse et al.
4,701,415 A 10/1987 Dutton et al.
(Continued)

FOREIGN PATENT DOCUMENTS

DE 102004049210 A1 6/2005
EP 2000529 A2 12/2008
(Continued)

OTHER PUBLICATIONS

Patent Abstracts of Japan, Publication No. 63-108262, Published on May 13, 1988, 1 page.

(Continued)

*Primary Examiner* — William H Beisner
(74) *Attorney, Agent, or Firm* — McDermott Will & Emery LLP

(57) ABSTRACT

A culture apparatus comprising: a fan configured to circulate air inside a culture chamber in a predetermined direction in the culture chamber; a duct configured to guide air circulating inside the culture chamber along a wall face inside the culture chamber from an upper part to a lower part of the culture chamber; and a gas generator detachable from a predetermined position at a lower part of the duct, the gas generator being configured to take in air discharged from a lower part of the duct and discharge together with the air taken in a hydrogen peroxide gas to sterilize the inside of the culture chamber generated from a hydrogen peroxide solution into the culture chamber.

2 Claims, 20 Drawing Sheets

(56) References Cited

U.S. PATENT DOCUMENTS

| | | | |
|---|---|---|---|
| 5,418,131 A | 5/1995 | Butts | |
| 5,616,115 A * | 4/1997 | Gloyd et al. | 600/22 |
| 5,792,427 A | 8/1998 | Hugh et al. | |
| 6,726,186 B2 * | 4/2004 | Gaaloul et al. | 261/81 |
| 8,083,999 B2 * | 12/2011 | Busujima | 422/298 |
| 2005/0084420 A1 | 4/2005 | Osawa et al. | |
| 2009/0227008 A1 * | 9/2009 | Busujima | 435/289.1 |

FOREIGN PATENT DOCUMENTS

| | | |
|---|---|---|
| EP | 2036458 A1 | 3/2009 |
| JP | 61-154800 U | 9/1986 |
| JP | 63-108262 A | 5/1988 |
| JP | 11-108871 A | 4/1999 |
| JP | 2004-000275 A | 1/2004 |
| JP | 2005-118021 A | 5/2005 |
| JP | 2005-274505 A | 10/2005 |
| JP | 2005-345146 A | 12/2005 |
| JP | 2007-259715 A | 10/2007 |
| WO | 2007111105 A1 | 10/2007 |
| WO | WO 2007111105 A1 * | 10/2007 |
| WO | 2008004533 A1 | 1/2008 |

OTHER PUBLICATIONS

Office Action issued in corresponding U.S. Appl. No. 13/527,027 dated Sep. 5, 2012 (9 pages).

Japanese Office Action issued in Japanese Patent Application No. 2008-181903 mailed on Apr. 2, 2013.

International Search Report for PCT/JP2009/064595 mailed Oct. 6, 2009 and Written Opinion of ISA for PCT/JP2009/064595 mailed Oct. 6, 2009 (9 pages).

Patent Abstracts of Japan, Publication No. 2004-000275, Published on Jan. 8, 2004, 1 page.

Office Action issued in correspondIng U.S. Patent No. 8,216,830 dated Oct. 6, 2011 (9 pages).

* cited by examiner

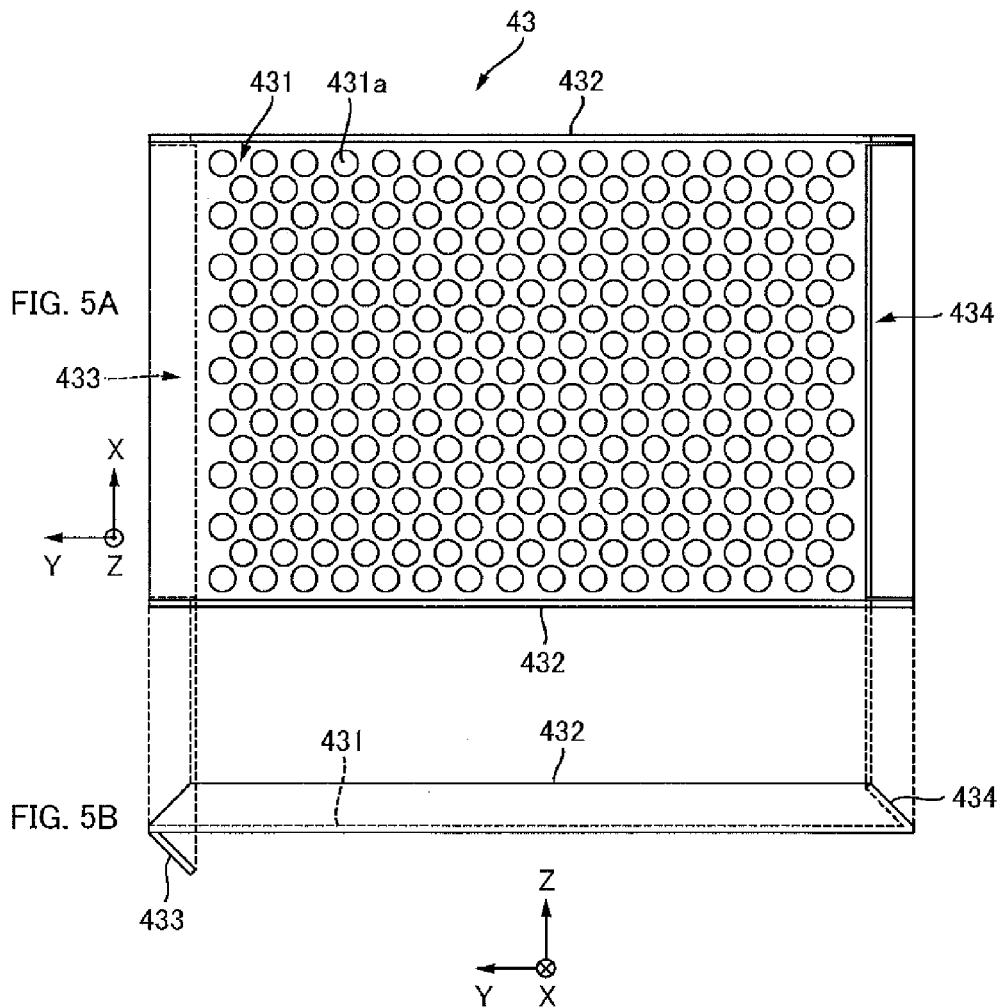

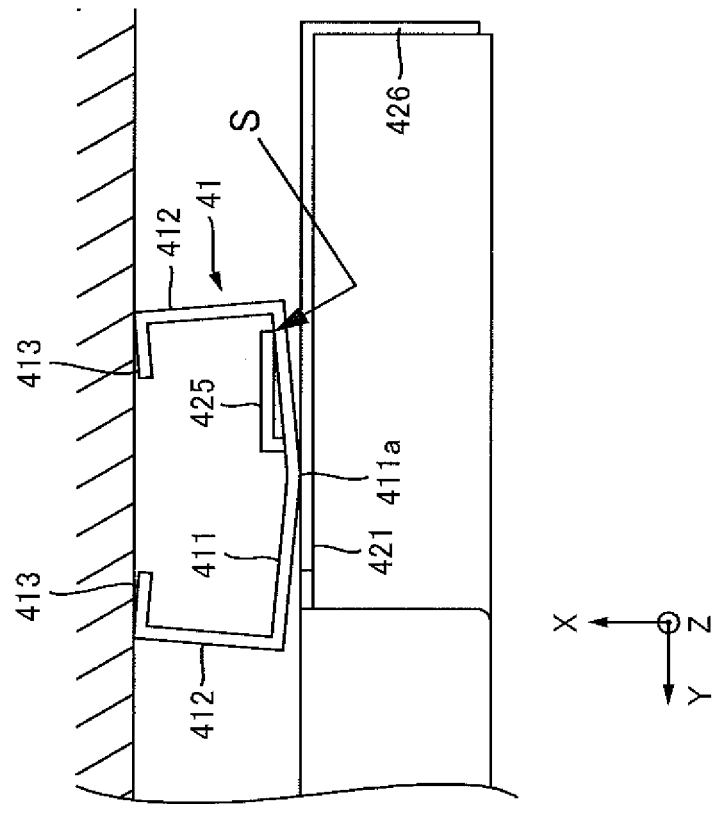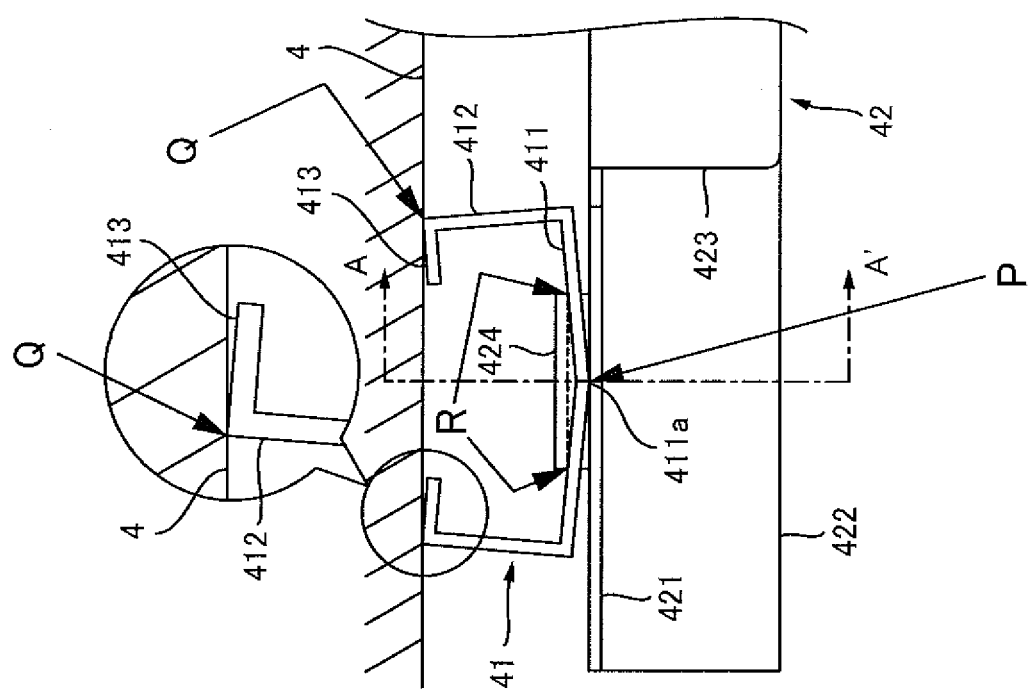
FIG. 7

CULTURE APPARATUS

CROSS-REFERENCE TO RELATED APPLICATIONS

This is a continuation of application Ser. No. 12/707,122 filed on Feb. 17, 2010, and issued as U.S. Pat. No. 8,216,830 on Jul. 10, 2012, which is a continuation application of International Patent Application No. PCT/JP2009/64595 filed Aug. 20, 2009, which claims the benefit of priority to Japanese Patent Application No. 2008-218615 filed Aug. 27, 2008. The full contents of the patent applications are incorporated herein by reference.

BACKGROUND OF THE INVENTION

1. Field of the Invention

The present invention relates to a culture apparatus.

2. Description of the Related Art

There is known a culture apparatus for culturing culture such as a cell, a microorganism and the like in a culture chamber, for example. This culture apparatus includes a fan for circulating air in the culture chamber and a duct for guiding the air circulating in the culture chamber from an upper part to a lower part in the culture chamber.

During culturing, by circulating the air in the culture chamber by the fan, gas such as carbon dioxide in the air in the culture chamber is maintained at uniform concentration or the inside of the culture chamber is maintained at a uniform temperature higher than outside air temperature, for example. Also, during culturing, the air discharged from the duct to the lower part using the fan as a driving power changes the direction of a current of the air upward on a water face of a humidification tray or the like placed on a bottom face of the culture chamber, for example, to form a rising air current, so that humidity is maintained in the culture arranged in this rising air current.

After the above culturing of the culture is finished, the inside of the culture chamber needs to be cleaned before starting another subsequent culturing of culture. Specifically, in order to disinfect the culture, bacteria caused by that, and the like, hydrogen peroxide ($H_2O_2$) gas with a sterilization effect might be generated so as to fill the inside of the culture chamber with the hydrogen peroxide gas with predetermined concentration, and such state might be maintained for a predetermined time. For this purpose, a gas generator for generating the hydrogen peroxide gas is disclosed (See Japanese Patent Laid-Open Publication No. 2007-259715, for example).

This gas generator includes a tank for storing hydrogen peroxide solution (aqueous solution in which hydrogen peroxide is dissolved) and an ultrasonic vibrator for generating gas by atomizing the hydrogen peroxide solution, and generates the hydrogen peroxide gas by vibration of the ultrasonic vibrator.

In a disinfecting process disclosed in Japanese Patent Laid-Open Publication No. 2007-259715, the humidification tray or the like, which have been used during culturing, is demounted from the bottom face of the culture chamber, the gas generator having a tank filled with the hydrogen peroxide solution is arranged on the bottom face, and the ultrasonic vibrator of the gas generator is operated for a predetermined time in the sealed culture chamber.

In a case where the above-mentioned gas generator is used for sterilization in the culture chamber, since the hydrogen peroxide gas has specific gravity greater than that of the air, there is a tendency that the hydrogen peroxide gas remains stationary in the lower part in the culture chamber by merely being atomized by the ultrasonic vibrator. If the hydrogen peroxide gas is not distributed in the culture chamber as above, the sterilization effect of the culture apparatus may be deteriorated.

On the other hand, if blowing means for discharging the hydrogen peroxide gas from the gas generator so as to have it distributed in the culture chamber is individually provided inside the gas generator, for example, there is a problem that the air blowing means is corroded by the hydrogen peroxide solution and easily fails. Thus, there is a fear that stability of the sterilization effect of the culture apparatus is deteriorated.

SUMMARY OF THE INVENTION

A culture apparatus according to an aspect of the present invention, comprises: a fan configured to circulate air inside a culture chamber in a predetermined direction in the culture chamber; a duct configured to guide air circulating inside the culture chamber along a wall face inside the culture chamber from an upper part to a lower part of the culture chamber; and a gas generator detachable from a predetermined position at a lower part of the duct, the gas generator being configured to take in air discharged from a lower part of the duct and discharge together with the air taken in a hydrogen peroxide gas to sterilize the inside of the culture chamber generated from a hydrogen peroxide solution into the culture chamber.

An embodiment of the present invention has an object to improve stability of the sterilization effect in the culture chamber by the culture apparatus.

Other features of the present invention will become apparent from descriptions of this specification and of the accompanying drawings.

BRIEF DESCRIPTION OF THE DRAWINGS

For more thorough understanding of the present invention and advantages thereof, the following description should be read in conjunction with the accompanying drawings, in which:

FIG. 5A is a diagram of a shelf plate in FIG. 1 viewed in the −Z direction,

FIG. 5B is a diagram of a shelf plate in FIG. 1 viewed in the +X direction;

FIG. 7 is a diagram of a shelf support and a shelf rest in FIG. 1 viewed in the −Z direction;

Figure 8:
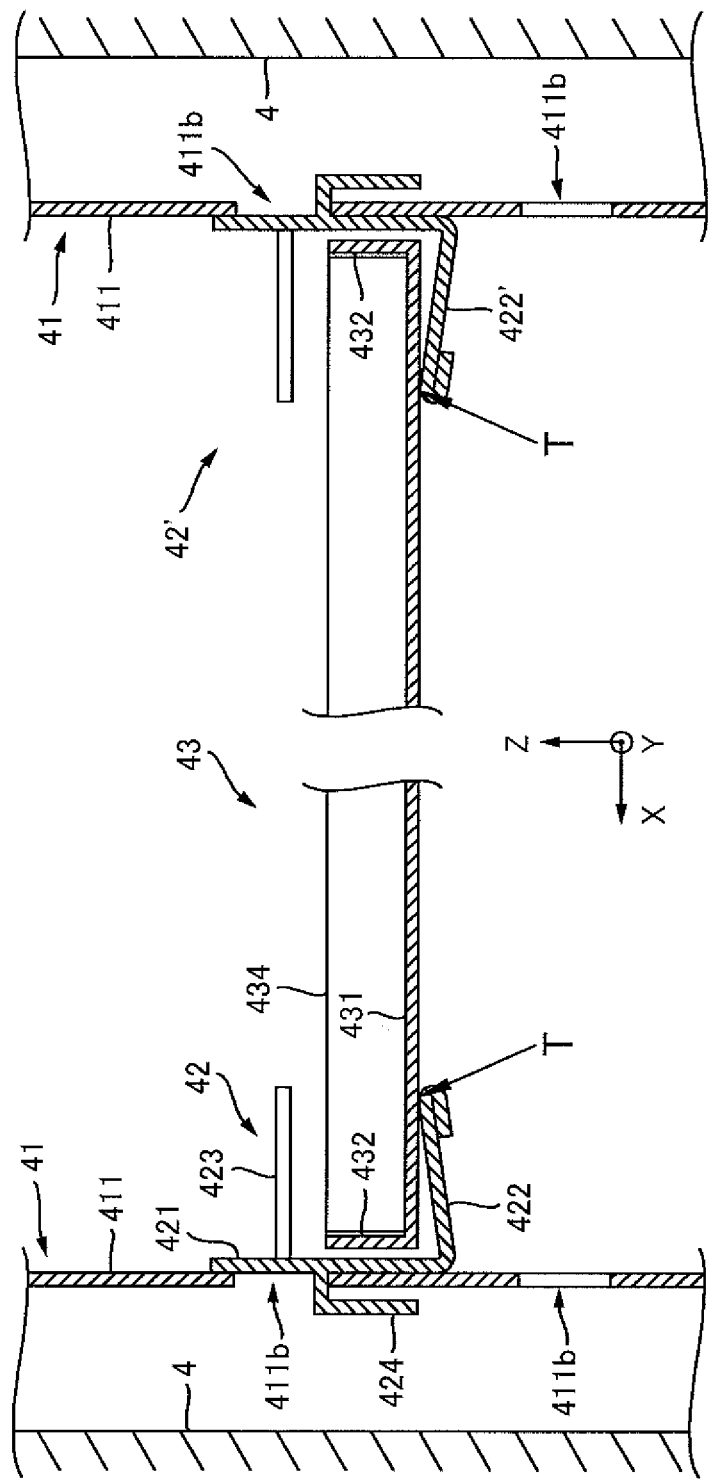
FIG. 8 is a cross sectional view illustrating cross sections of an inner face of an inner box, a shelf support and a shelf rest
Figure 9:
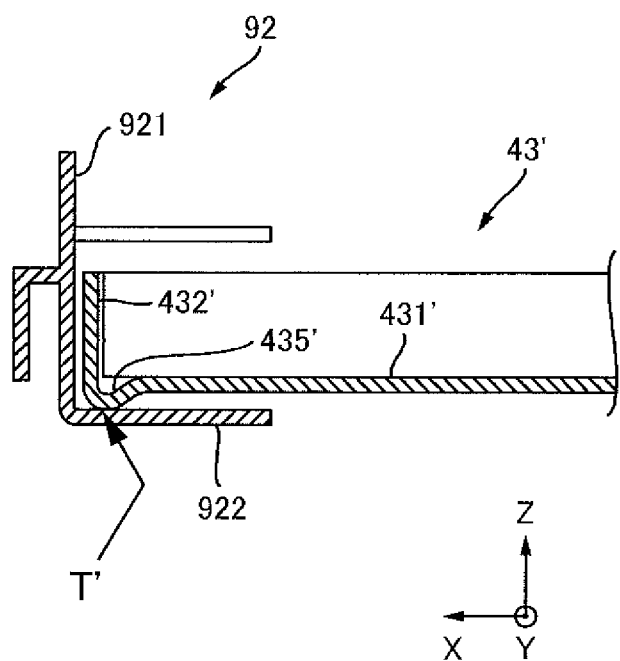
Figure 10:
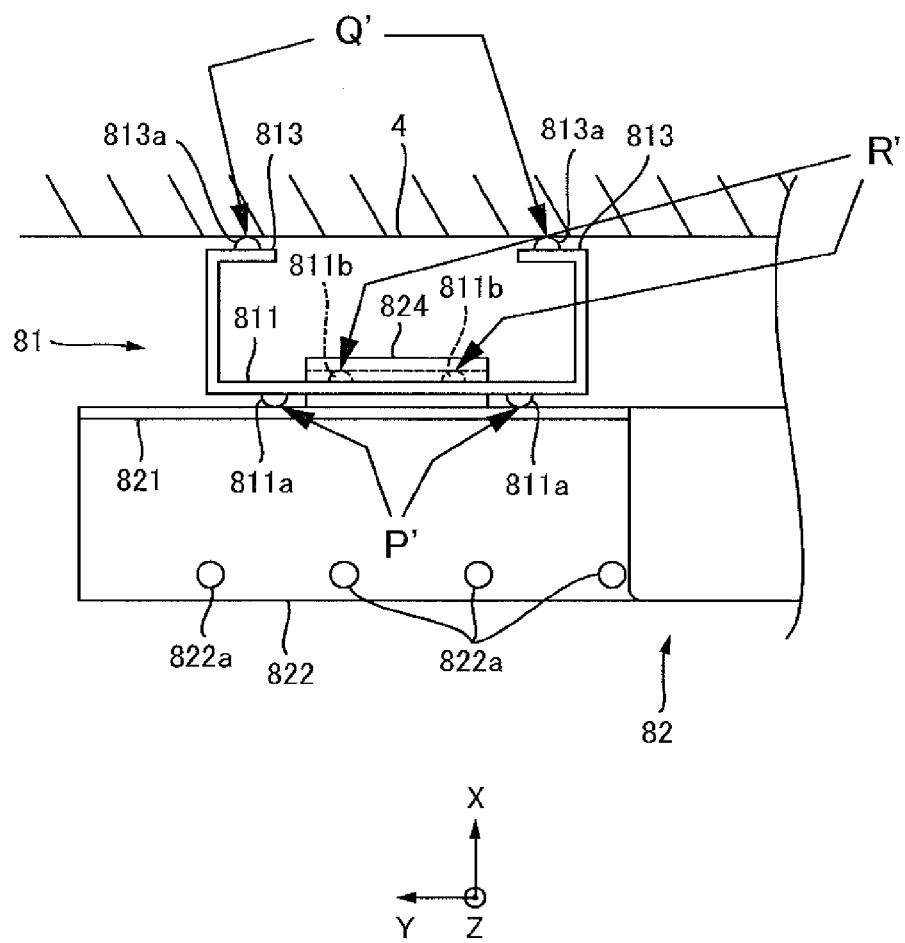
Figure 11:
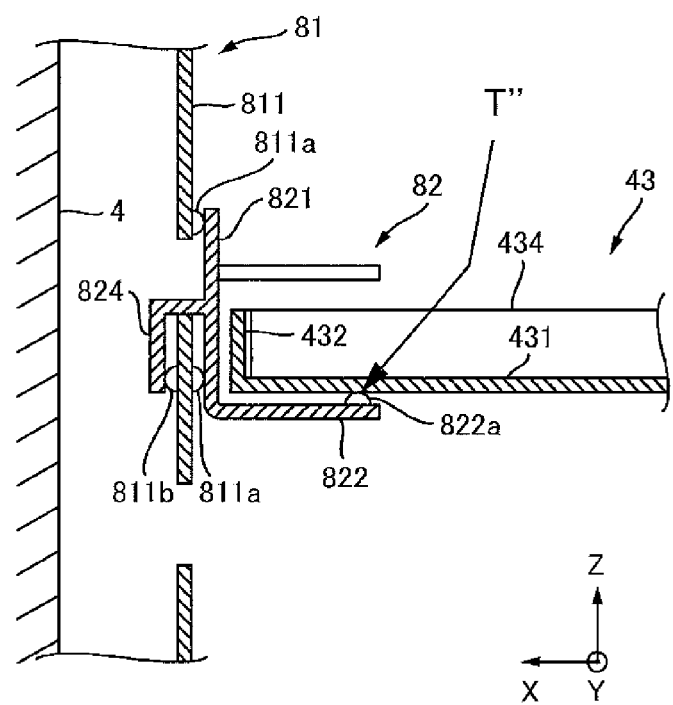
Figure 12:
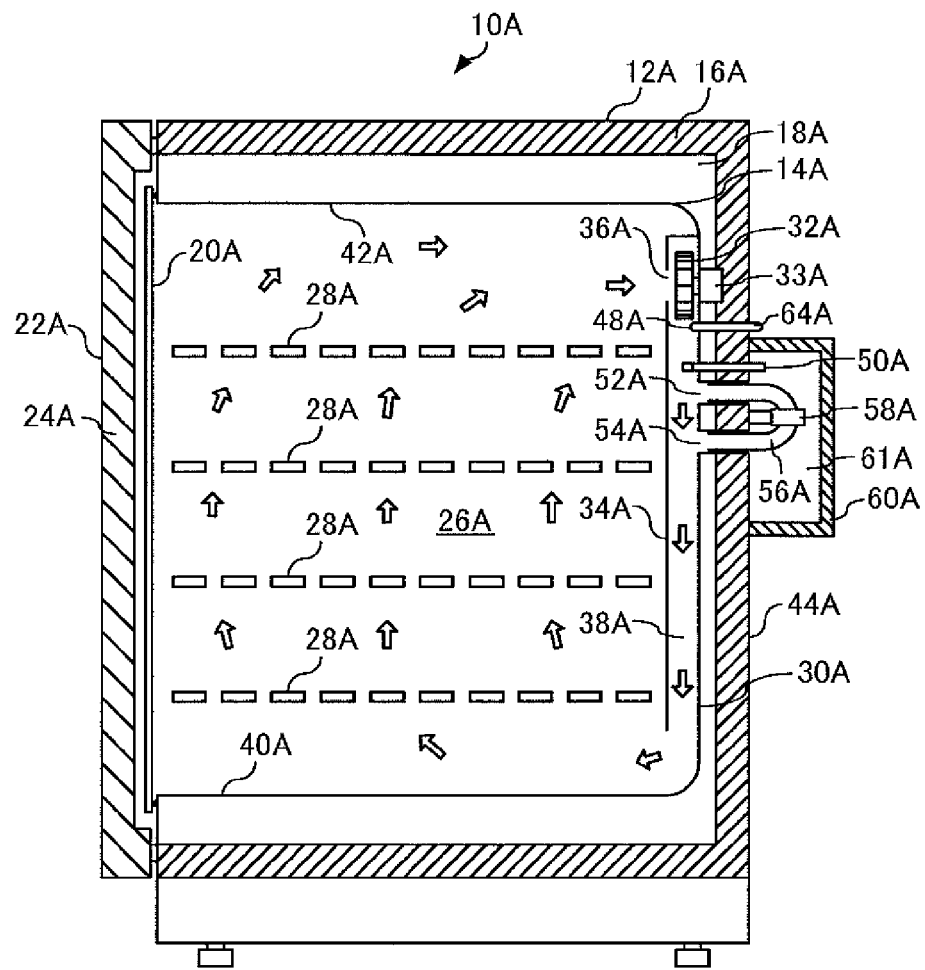
Figure 13:
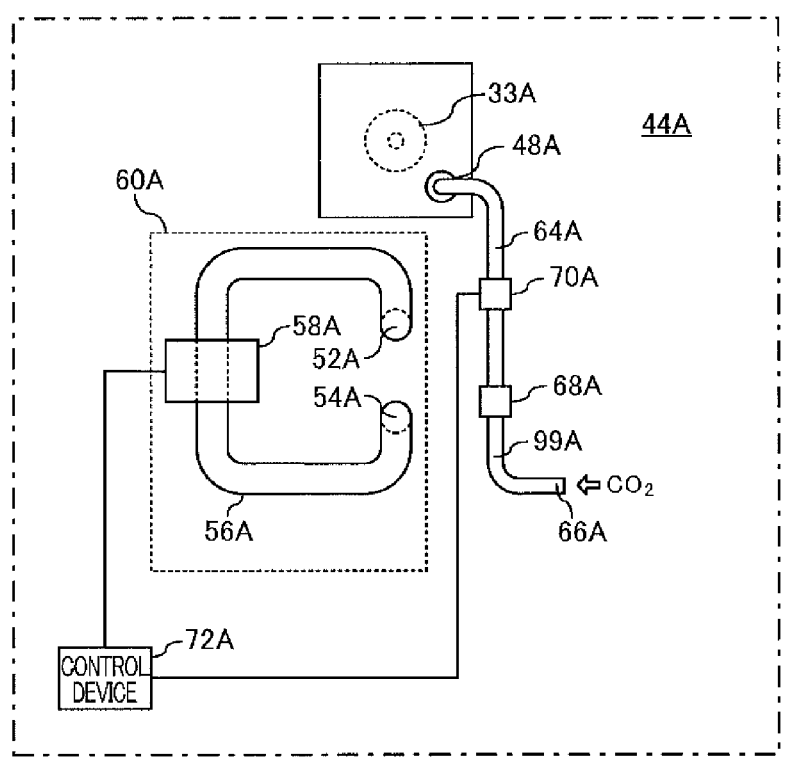
Figure 14:
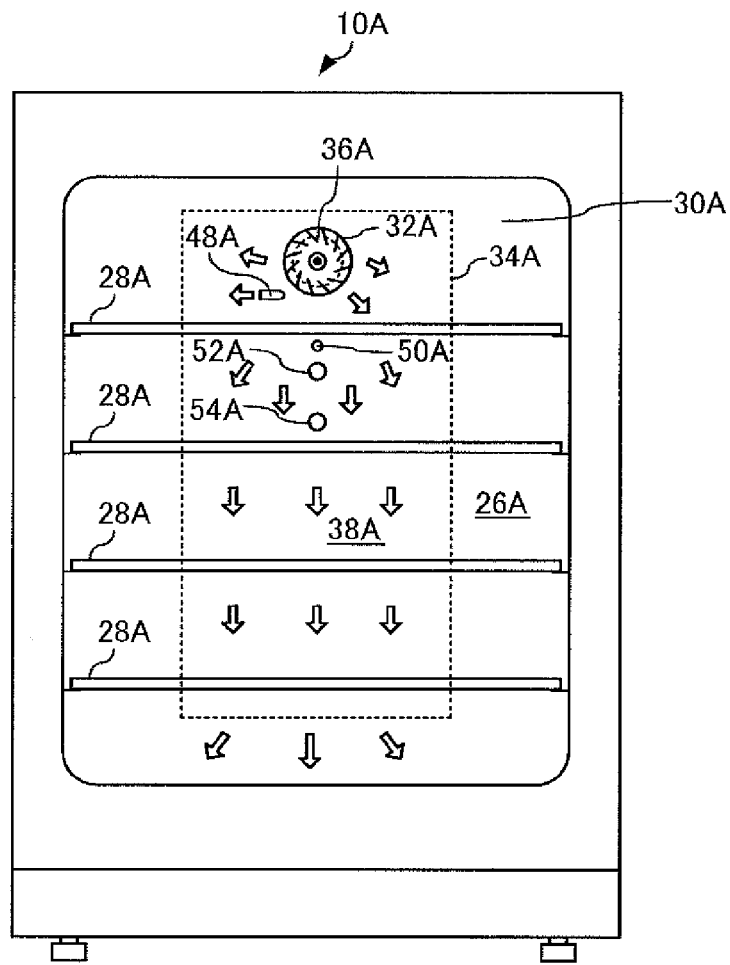
Figure 15:
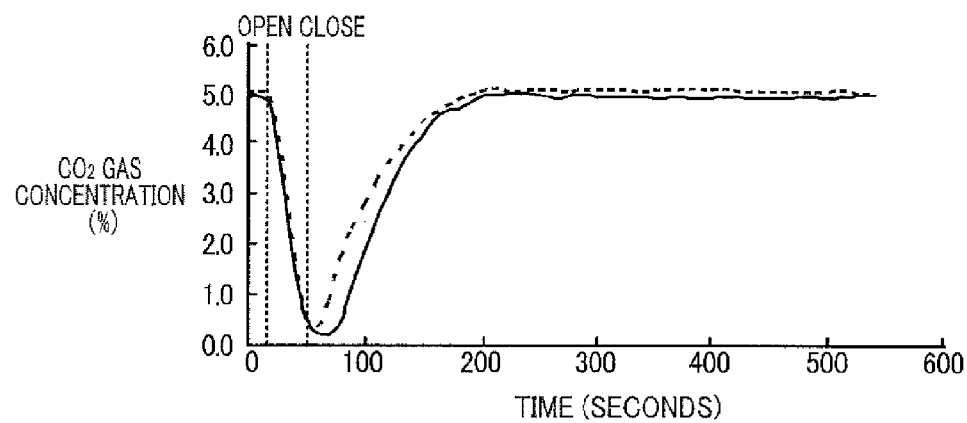
Figure 16:
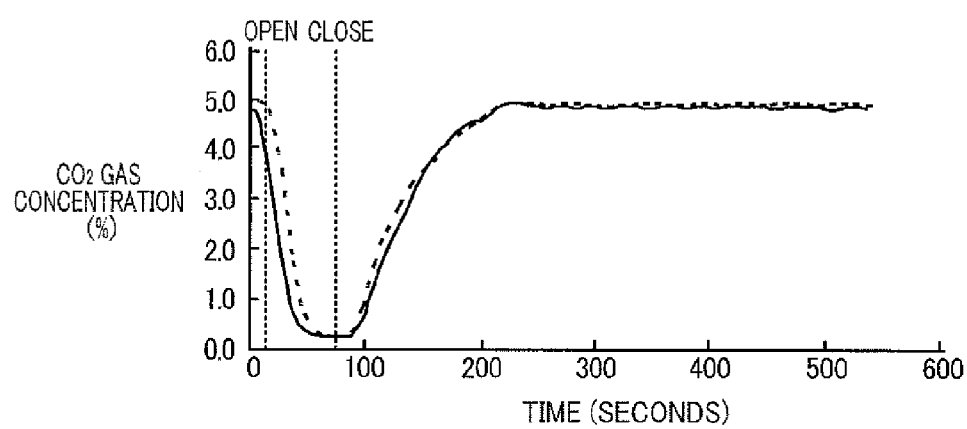
Figure 17:
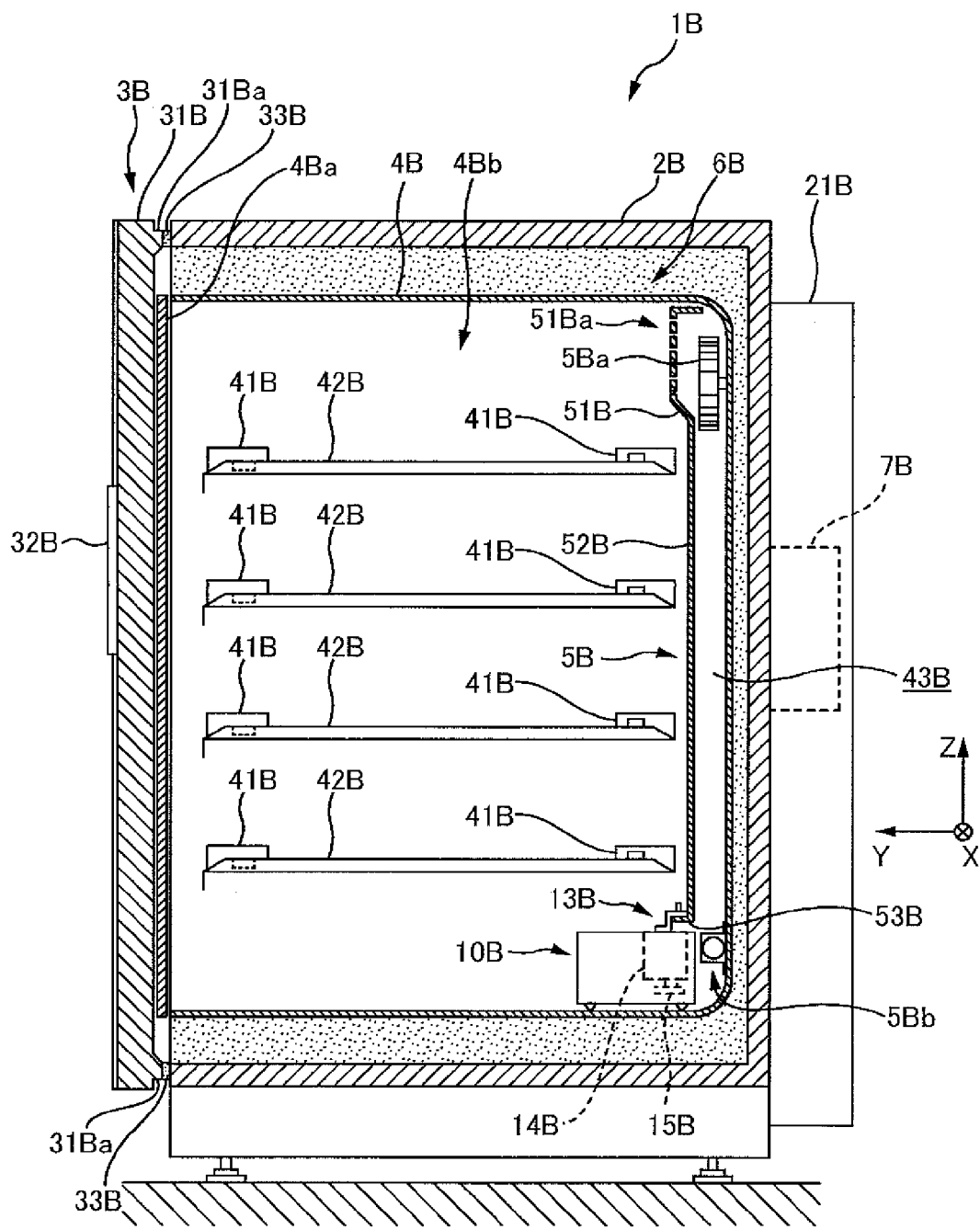
Figure 19:
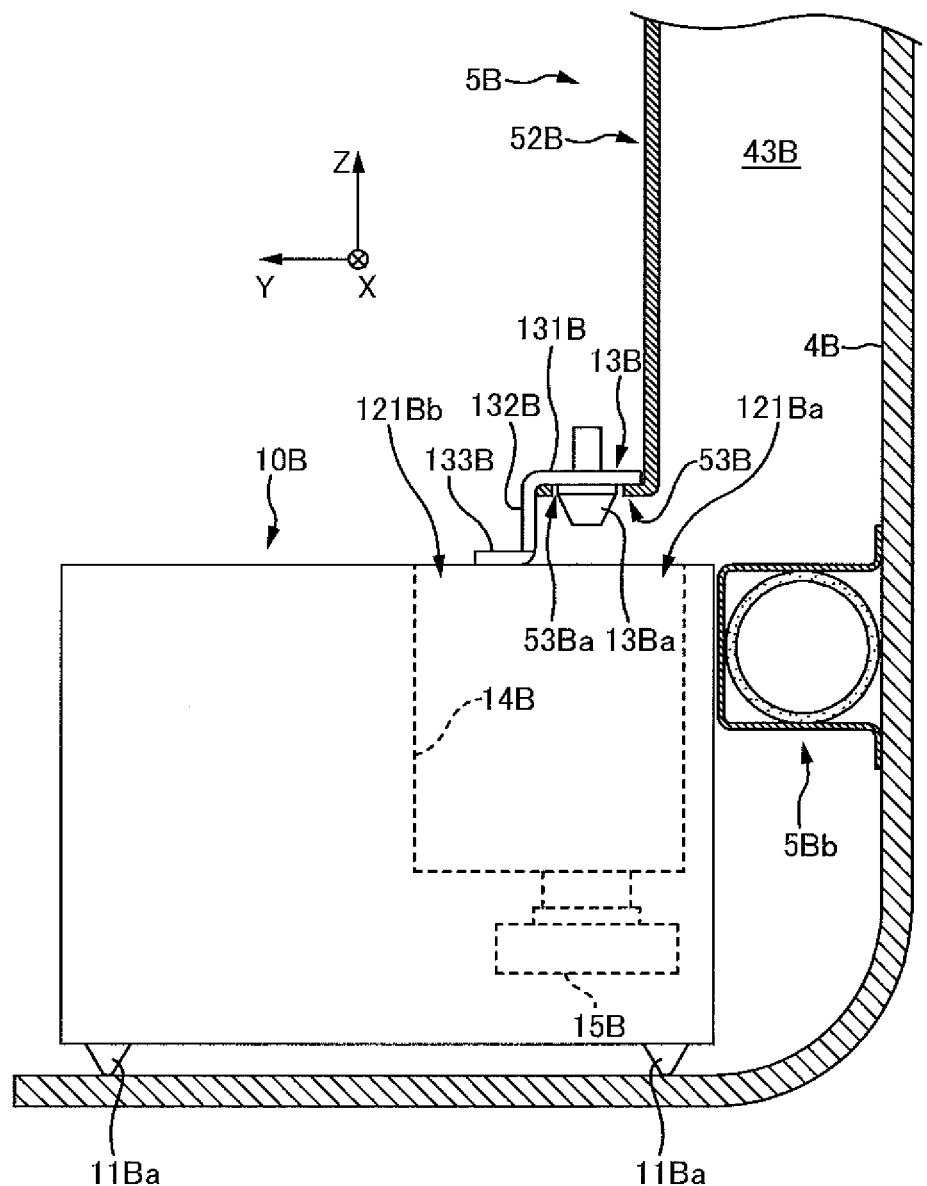
Figure 20:
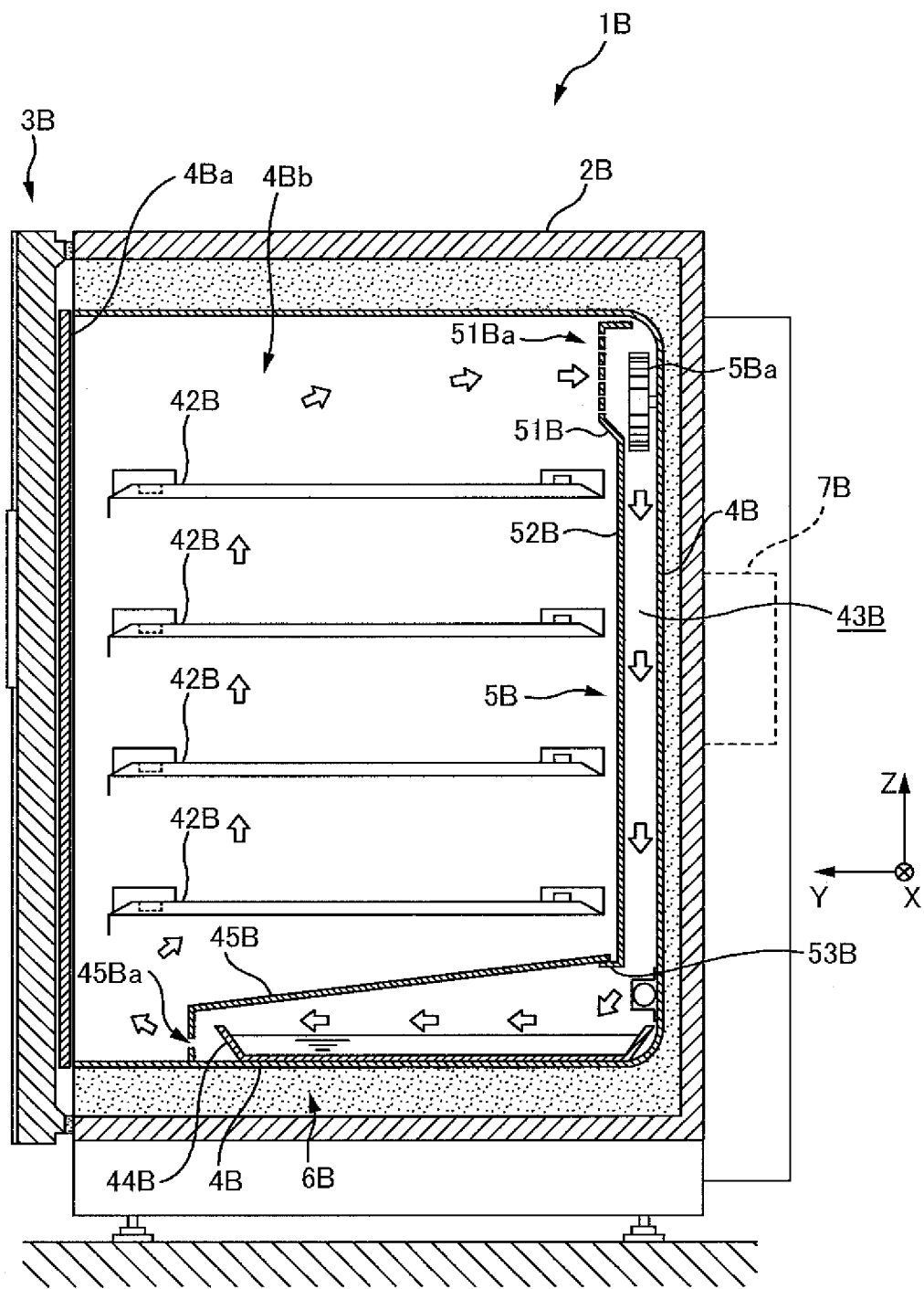
Figure 21:
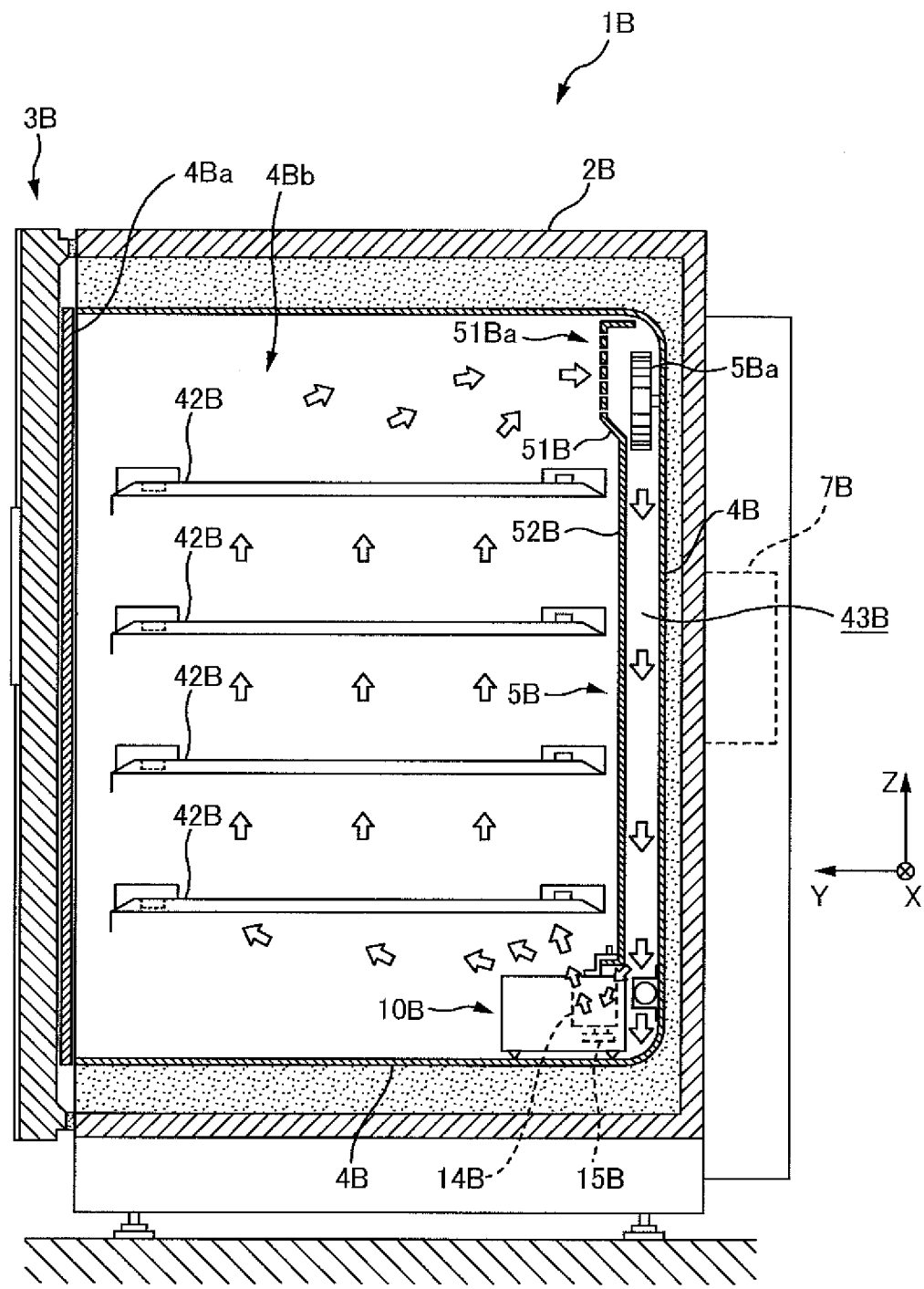

42 on an A-A' line in FIG. 7 and cross sections of the shelf plate and a shelf rest 42' in the same cross section;

FIG. 9 is a cross sectional view of a shelf rest and a shelf plate in cross section similar to that in FIG. 8;

FIG. 10 is a diagram of an inner face of an inner box, a shelf support and a shelf rest viewed from a direction similar to that in a case of FIG. 7;

FIG. 11 is a cross sectional view of an inner face of an inner box, a shelf support, a shelf rest, and a shelf plate in cross section similar to that in FIG. 8;

FIG. 12 is a cross sectional view of a culture apparatus according to a second embodiment of the present invention;

FIG. 13 is a diagram illustrating a part of a back face of an outer box of a culture apparatus;

FIG. 14 is a front view in a state where an outer door and an inner door of a culture apparatus are opened;

FIG. 15 is an experimental result illustrating an example of $CO_2$ gas concentration when an outer door and an inner door have been opened for 30 seconds;

FIG. 16 is an experimental result illustrating an example of $CO_2$ gas concentration when an outer door and an inner door have been opened for 60 seconds;

FIG. 17 is a side sectional view of an example of a culture apparatus according to a third embodiment of the present invention;

FIG. 18A is a plan view of an example of a gas generator according to a third embodiment of the present invention, FIG. 18B is a partial sectional view of a gas generator on an A-A' line in FIG. 18A;

FIG. 19 is an enlarged view of a gas generator in FIG. 17 and in the vicinity thereof;

FIG. 20 is a schematic diagram illustrating an example of an air passage in a culture chamber during culturing of a culture apparatus in FIG. 17; and FIG. 21 is a schematic diagram illustrating an example of an air passage in a culture chamber during sterilizing of a culture apparatus in FIG. 17.

DETAILED DESCRIPTION OF THE INVENTION

At least the following details will become apparent from descriptions of this specification and of the accompanying drawings.

First Embodiment

There is known a culture apparatus for culturing a culture such as a cell, a microorganism, for example, in a culture chamber. Such culture apparatus includes a shelf plate on which the culture is placed, a shelf rest for holding the shelf plate horizontally, and a plurality of shelf supports for holding the shelf rest horizontally, inside the culture chamber, for example (See Japanese Patent Laid-Open Publication No. 2004-275, for example).

Before subsequent culturing is started after culturing, the inside of the culture chamber needs to be cleaned. Thus, while leaving the shelf plate, the shelf rest, and the shelf supports used for the previous culturing as they are, sterilizing gas such as hydrogen peroxide ($H_2O_2$) gas, for example, is circulated by a fan in the culture chamber so as to disinfect bacteria caused by the previous culturing, and adhering to members relating to the shelves, an inner face of the culture chamber and the like (See Japanese Patent Laid-Open Publication No. 2007-259715, for example).

Since there is a location where the sterilizing gas can hardly distribute due to plane contact between the above-mentioned shelf plates and the shelf rests, the sterilization at this location might be insufficient. Thus, there is a fear that a sterilization effect of the culture apparatus might be deteriorated.

An embodiment has an object to allow sterilizing gas to be easily distributed to a shelf plate and a shelf rest and further to a portion where the shelf rest and a shelf support are in contact with each other.

<Configuration of a Culture Apparatus>

Figure 1:
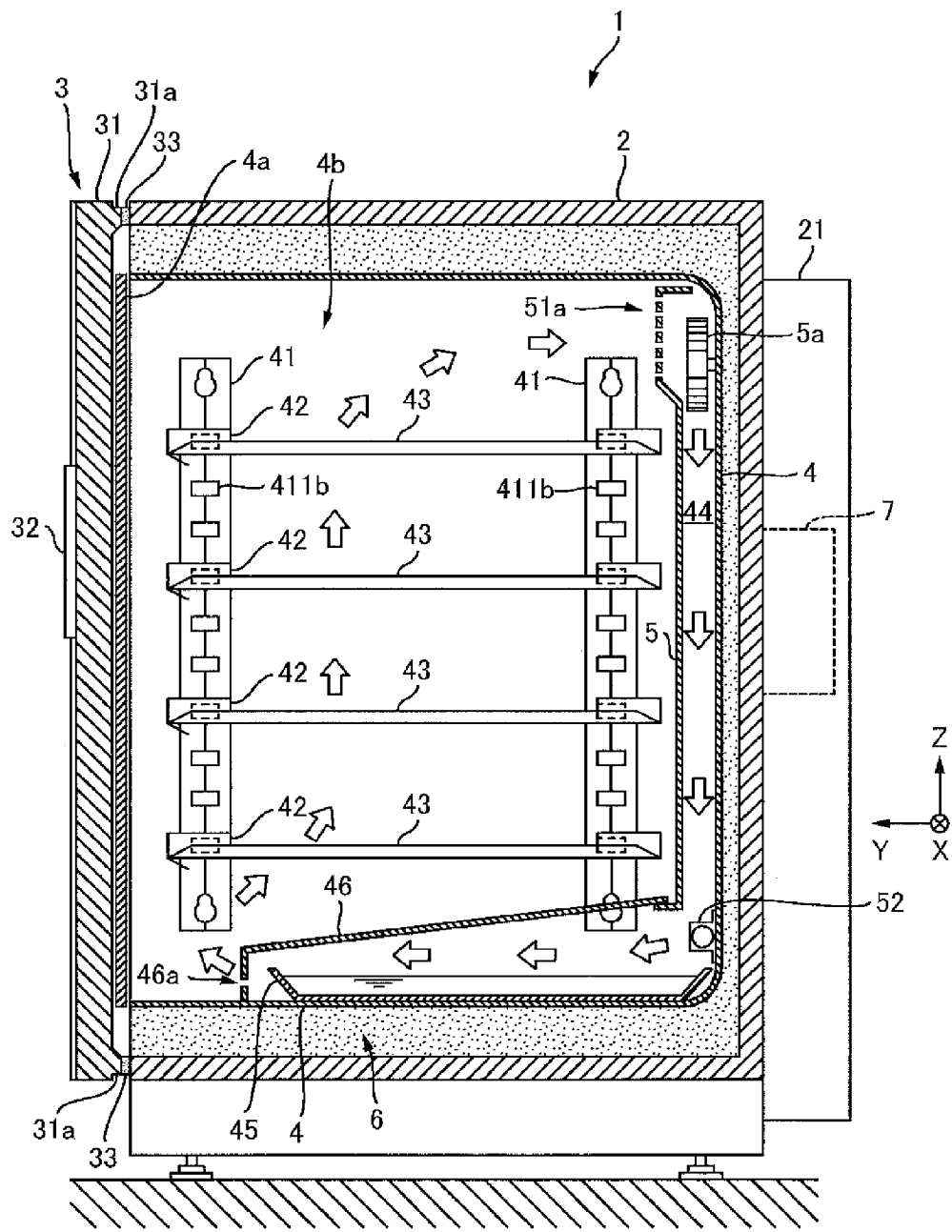
FIG. 1 is a side sectional view of an example of a culture apparatus according to a first embodiment of the present invention.
Figure 2:
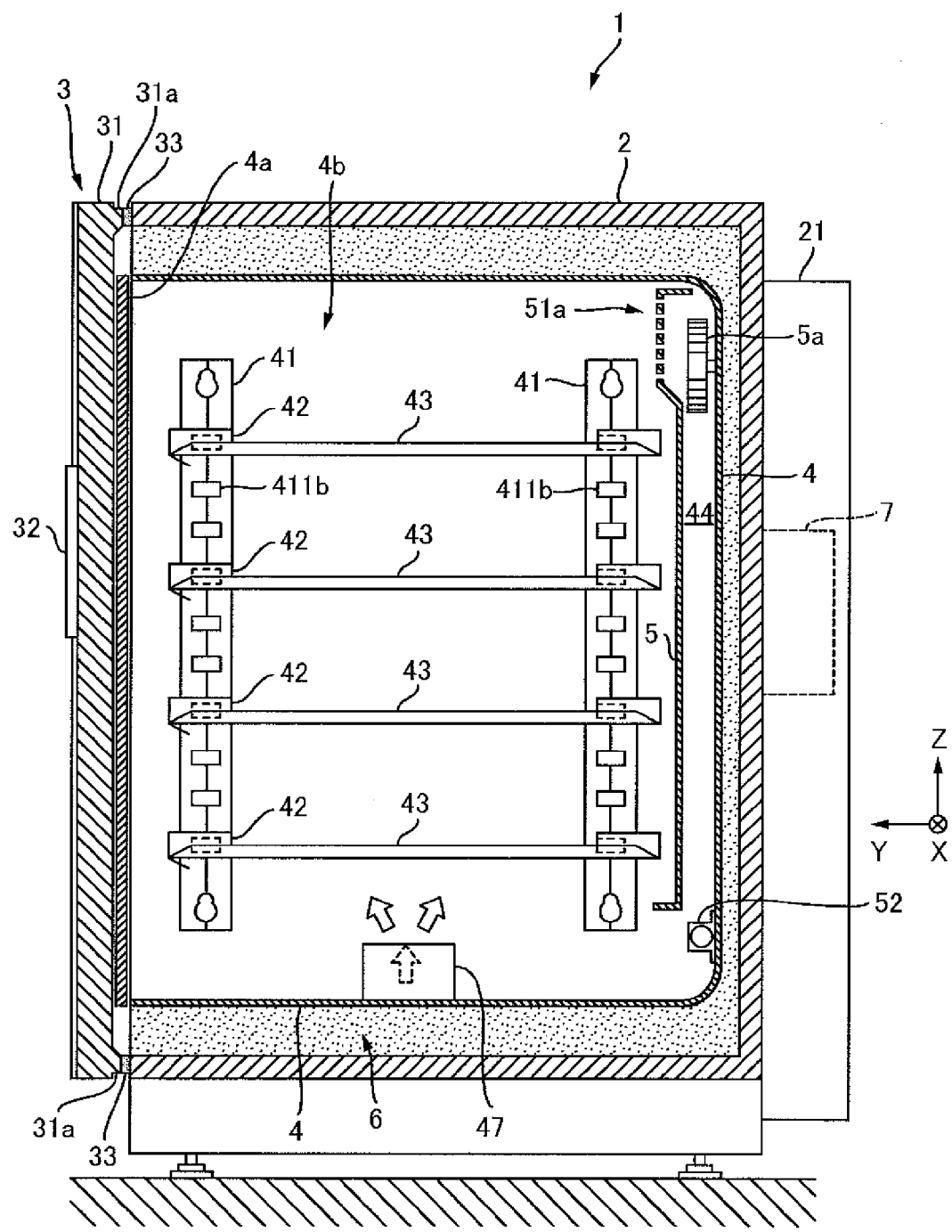
FIG. 2 is a side sectional view of a configuration example of a culture apparatus 1 in FIG. 1 when a sterilizing operation is performed.

A configuration example of a culture apparatus 1 according to a first embodiment of the present invention will be described referring to FIGS. 1 and 2. FIG. 1 is a side sectional view of a configuration example of the culture apparatus 1 according to a first embodiment of the present invention, and FIG. 2 is a side sectional view of a configuration example of the culture apparatus 1 in FIG. 1 when a sterilizing operation is performed.

As exemplified in FIG. 1, the culture apparatus 1 includes a shelf plate 43, a shelf rest 42, and a shelf support 41 in a culture chamber 4b. In this culture chamber 4b, culture such as a cell, a microorganism is cultured.

The culture chamber 4b is formed inside an inner box 4, and this inner box 4 is housed inside an outer box 2 in such a state as to be insulated from outside air. The inner box 4 is a substantially rectangular solid shaped box made of stainless steel, for example, and the outer box 2 is a box substantially in a shape similar to the inner box 4 made of stainless steel, for example. On an opening on a front side (+Y side) of the inner box 4, an inner door 4a is provided openable/closable through a predetermined hinge (not shown). This inner door 4a is in a flat-plate shape made of tempered glass, for example, and when it is closed through packing (not shown) with respect to the opening of the inner box 4, the inside of the inner box 4 is made air tight against the outside. On an opening on a front side of the outer box 2, an outer door 3 is provided in such a manner as to be openable/closable through a predetermined hinge (not shown). This outer door 3 is in a flat-plate shape and made of metal, for example.

The shelf plate 43 is a plate member which is made of stainless steel, for example, and on which culture is placed.

The shelf rest 42 is a member made of stainless steel, for example, for supporting the shelf plate 43 and for holding the shelf plate 43 horizontally (in parallel with the XY plane) and is disposed on one side face side (+X side) of the culture chamber 4b so that the longitudinal direction thereof is in the horizontal direction (Y-axis direction). This shelf rest 42 and a shelf rest 42' (See FIG. 8, which will be described later) disposed on the other side face side (-X side) of the culture chamber 4b have mirror-symmetrical shapes mutually mirror-symmetrical with respect to a plane (not shown) at the center between the side faces opposing to each other in the culture chamber 4b and in parallel with the side faces. In other words, the shelf rests 42 and 42' are provided in a pair on the right side and the left side in the X direction to support the shelf plate 43. Hereinafter, description of the shelf rest 42' will be omitted as it is similar to the description of the shelf rest 42 except description referring to FIG. 8, which will be described later.

The shelf support 41 is a member made of stainless steel, for example, which horizontally supports the shelf rests 42 so as to be disposed on the ±X sides of the inner box 4, and two of which, for example, are disposed on each of the inner faces on the ±X sides so that the longitudinal direction thereof is in a perpendicular direction (Z-axis direction). The shelf support 41 has a plurality of fitting-in holes 411b in the longitudinal direction thereof with a predetermined space between the holes, for example, so that the shelf rests 42 can be locked through the fitting-in holes 411b.

On an inner face of the outer box 2, an insulating material (not shown) for thermal insulation is provided, and an air jacket 6 is formed between the insulating material and the inner box 4, as an air circulation path, for example, for further thermal insulation. On the air jacket 6, a heater (not shown) for adjusting a temperature inside the culture chamber 4b is mounted. On an outer face on the rear side (−Y side) of the outer box 2, a sensor box 7 is provided which includes a sensor (not shown) for detecting a temperature inside the culture chamber 4b, a nozzle (not shown) for injecting gas such as carbon dioxide into the culture chamber 4b, a sensor (not shown) for detecting concentration of carbon dioxide or the like in the culture chamber 4b and the like, for example. The nozzle and the sensor are mounted from the outside of the outer box 2 through a hole (not shown) drilled from the outer face on the rear side of the outer box 2 to the inner face on the rear side of the inner box 4, for example. The sensor is electrically connected to a control board (not shown) through wiring (not shown), for example. The outer face and the sensor box 7 on the rear side of the outer box 2 are covered by a cover 21 including an insulating material (not shown) inside.

The outer door 3 includes a door main body 31 made of metal provided inside with an insulating material (not shown) for thermal insulation, a heater (not shown) for adjusting the temperature in the culture chamber 4b and the like, and packing 33 mounted on a projection portion 31a opposing the opening of the outer box 2 in the door main body 31. The outer door 3 further includes a control panel 32 on the front side of the door main body 31. The control panel 32 includes a key (not shown) for setting a temperature, concentration of carbon dioxide and the like in the culture chamber 4b and a display (not shown) for displaying their current values.

Moreover, a wall on the rear side of the inner box 4 and a wall plate 5 made of stainless steel, for example, make up a duct 44 for forming an air passage. At an upper part in the duct 44 (+Z side), a fan 5a (sirocco fan) is provided, and at a lower part (−Z side), an ultraviolet lamp 52 is provided for sterilizing bacteria contained in air passing through the duct 43 and bacteria contained in water for humidification in a humidification tray 45 arranged at the bottom of the duct 43.

As exemplified by framed arrows in FIG. 1, when culture is cultured in the culture chamber 4b, by rotation in a predetermined direction of the fan 5a, air on the shelf plate 43 side at the upper part in the culture chamber 4b flows into the duct 44 through an intake 51a, flows from the upper part to the lower part in the duct 44, and is humidified by the water for humidification in the humidification tray 45, and then, the humidified air passes through holes 46a on the front side of a cover 46 and returns to the shelf plate 43 side. By such circulation of air, the inside of the culture chamber 4b is maintained at substantially uniform temperature, humidity, and gas concentration such as carbon dioxide.

As shown in FIG. 2, when the inside of the culture chamber 4b is sterilized, the humidification tray 45 and the cover 46 are demounted from a bottom face of the culture chamber 4b, a gas generator 47 is placed, and while hydrogen peroxide gas, for example, is generated by the generator, the fan 5a in the duct 44 is rotated in the predetermined direction. The gas generator 47 includes a tank (not shown) for storing hydrogen peroxide solution (aqueous solution in which hydrogen peroxide gas is dissolved) and an ultrasonic vibrator (not shown) for atomizing the hydrogen peroxide solution in the tank, for example.

<Configuration of Shelf Support/Shelf Rest/Shelf Plate>

Figures 3A, 3B:
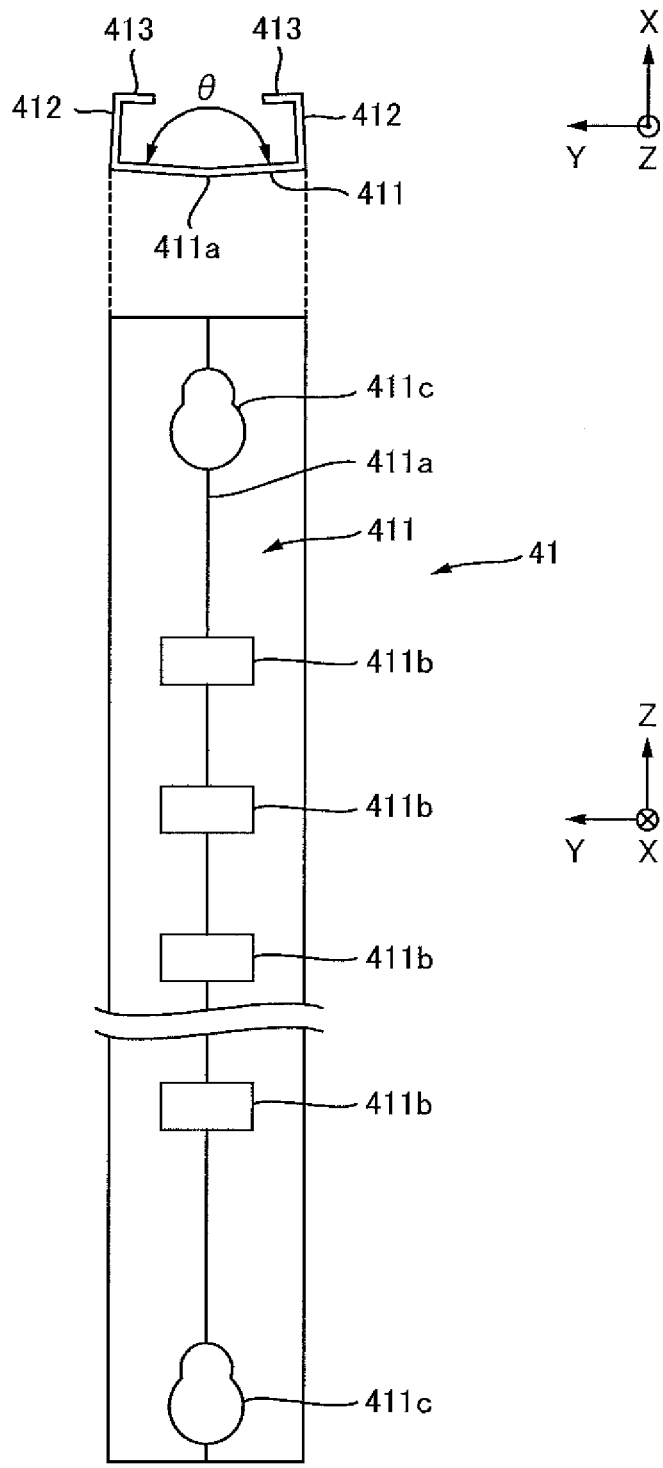
FIG. 3A is a diagram of a shelf support in FIG. 1 viewed in the −Z direction.
FIG. 3B is a diagram of a shelf support in FIG. 1 viewed in the +X direction.
Figures 4A, 4B, 4C:
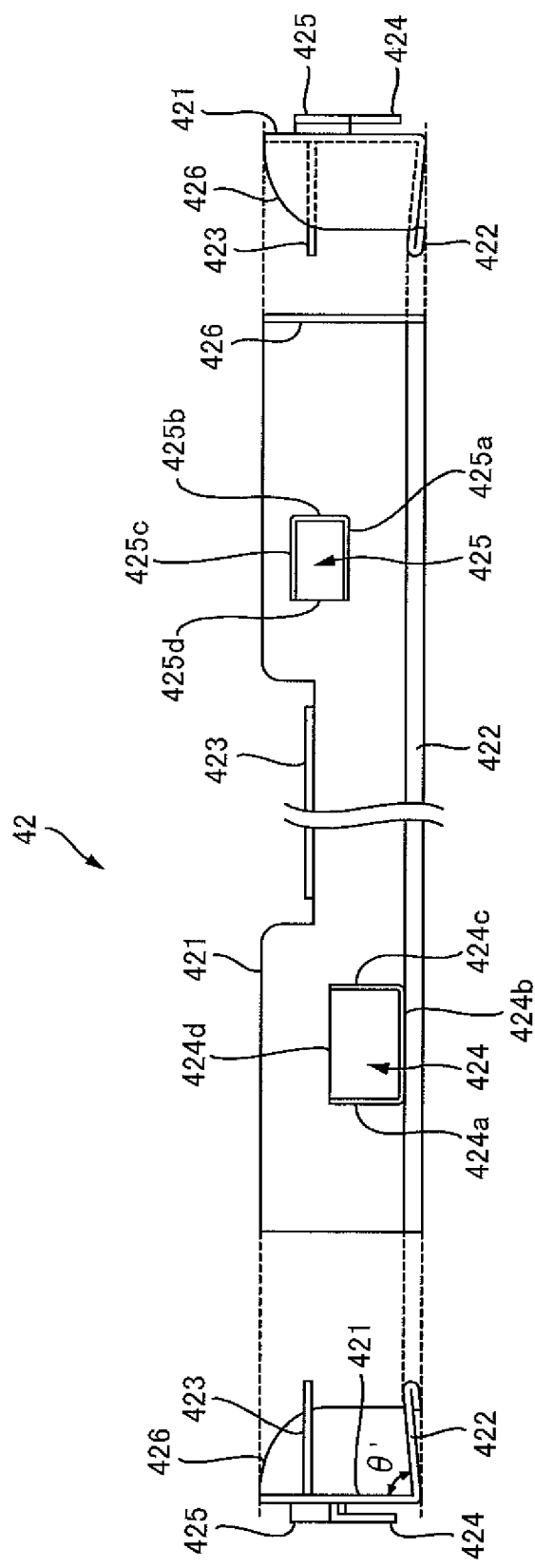
FIG. 4A is a diagram of a shelf rest in FIG. 1 viewed in the −Y direction.
FIG. 4B is a diagram of a shelf rest in FIG. 1 viewed in the +X direction.
FIG. 4C is a diagram of a shelf rest in FIG. 1 viewed in the +Y direction.

Referring to FIGS. 3 to 5, configuration examples of the above-mentioned shelf support 41, the shelf rest 42, and the shelf plate 43 will be described in detail. FIG. 3A is a diagram of the shelf support 41 in FIG. 1 viewed in the −Z direction, FIG. 3B is a diagram of the shelf support 41 in FIG. 1 viewed in the +X direction. FIG. 4A is a diagram of the shelf rest 42 in FIG. 1 viewed in the −Y direction, FIG. 4B is a diagram of the shelf rest 42 in FIG. 1 viewed in the +X direction, and FIG. 4C is a diagram of the shelf rest 42 in FIG. 1 viewed in the +Y direction. FIG. 5A is a diagram of the shelf plate 43 in FIG. 1 viewed in the −Z direction, and FIG. 5B is a diagram of the shelf plate 43 in FIG. 1 viewed in the +X direction.

<Shelf Support>

As exemplified in FIGS. 3A and 3B, the shelf support 41 is formed by performing drilling and bending work for a single plate member, for example. This shelf support 41 includes a bent plate (bent plate) 411, a pair of side pieces 412, and a pair of contact pieces 413.

The bent plate 411 is a plate-shaped member which is bent at a center line 411a in the width direction (Y-axis direction) orthogonal to the longitudinal direction thereof (Z-axis direction) so as to form mountain folding when viewed in a direction from the bent plate 411 to the contact piece 413. An angle of bend θ shown in FIG. 3A is 170 degrees, for example. As exemplified in FIG. 3B, the bent plate 411 has a plurality of rectangular fitting-in holes 411b along the center line 411a with the predetermined space between the holes, for example. As exemplified in FIG. 3B, the bent plate 411 has a hole 411c at each of both end portions in the Z-axis direction, the hole having a shape in which circles with centers displaced and diameters different from each other are overlapped. By fitting predetermined projection members not shown) from the inner face of the inner box 4 into these holes 411c, the shelf support 411 is detachably disposed on the inner face.

The side pieces 412 in a pair are plate-shaped members that are connected in a bending manner from both side ends in the Y-axis direction of the bent plate 411, respectively, and extend substantially in the X-axis direction. In the exemplification of FIG. 3A, the side pieces 412 in a pair each extends in such a direction that a space between the both side pieces in the Y-axis direction gets narrower as the pieces get closer to the side face of the culture chamber 4b from the bent plate 411.

The contact pieces 413 in a pair are plate-shaped members that are connected in a bending manner from the end portions on the side of the side pieces 412 not connected to the bent plate 411 and extend substantially in the Y-axis direction. In the exemplification of FIG. 3A, contact pieces 413 in a pair extend in such a direction as to become away from the side face of the culture chamber 4b toward the center side in the Y-axis direction from the side pieces 412 connected to the contact pieces 413.

Therefore, as obvious from FIG. 3A, the shelf support 41 has the side face on the side supporting the shelf rests 42 and 42' in a pair, which side face is in a shape of chevron in a cross-sectional manner whose point is in the center of the side face, and the shelf support 41 has the side face on the side supporting the shelf rests 42 and 42' in a pair, which side face is bent at the center.

<Shelf Rest>

As exemplified in FIGS. 4A, 4B, and 4C, the shelf rest 42 is formed by performing drilling and bending work for a single plate member, for example. This shelf rest 42 includes a vertical plate 421 (the other piece) and a rest piece 422 (one piece). Also, this shelf rest 42 includes a guide piece 423, a pair of locking piece 424 and a locking piece 425, and a stop piece 426.

The vertical plate 421 is a plate-shaped member having both end portions in the longitudinal direction wider in width in the vertical direction (Z-axis direction) than the center portion, and is supported by the shelf support 41.

The rest piece 422 is a plate-shaped member that is connected to the lower end of the vertical plate 421 in a bending manner in a direction away from the side face of the culture chamber 4b (that is, in such a direction as to get closer to the shelf plate 43) (−X direction), and extends from the side face of the culture chamber 4b toward the inside at an angle θ', to support the shelf plate 43. The angle of bend θ' shown in FIG. 3A is 80 degrees, for example. That is, the pair of shelf rests 42 and 42' each is, as obvious from FIG. 4A, in an L-shape in a cross-sectional manner, whose angle between the vertical plate 421 and the rest piece 422 is an acute angle.

The guide piece 423 is a plate-shaped member that is connected to the upper end (+Z side end) of the vertical plate 421 in a bending manner in a direction away from the side face of the culture chamber 4b, and extends in an orthogonal manner relative to the vertical plate 421.

The locking piece 424 is a tongue piece, which is formed with gaps 424a, 424b, and 424c on three sides at an end portion on the front side (+Y side) of the vertical plate 421 and is connected at a fold line 424d on one side, and this tongue piece is folded in such a direction (+X direction) as to get closer to the side face of the culture chamber 4b at the fold line 424d, and extends in the vertical direction forming an L-shape.

The locking piece 425 is a tongue piece, which is divided by gaps 425a, 425b, and 425c on three sides at an end portion on the rear side (−Y side) of the vertical plate 421 on the back side of the culture chamber 4b and is connected at a fold line 425d on one side, and this tongue piece is folded in such a direction (+X direction) as to get closer to the side face of the culture chamber 4b at the fold line 425d, and extends in the fore-and-aft direction forming an L-shape.

By fitting these locking pieces 424 and 425 whose hooked shapes are different in direction from each other into the fitting-in holes 411b of the two front and rear shelf supports 41 of the culture chamber 4b, the shelf rest 42 is prevented from coming off from the shelf support 41.

The stop piece 426 is a plate-shaped member that is connected to the rear side end in the vertical plate 421 in a bending manner in a direction away from the side face of the culture chamber 4b, and extends in the orthogonal manner relative to the vertical plate 421.

<Shelf Plate>

As exemplified in FIGS. 5A and 5B, the shelf plate 43 is formed by performing drilling and bending work for a single plate member, for example. This shelf plate 43 includes a bottom plate 431, a side piece 432, a front piece 433, and a back piece 434.

The bottom plate 431 is a flat-plate member, the side pieces 432 in a pair are plate-shaped members connected to the ±X side ends of the bottom plate 431 and formed by bending upward (+Z side) at a right angle, the front piece 433 is a plate-shaped member connected to the +Y side end of the bottom plate 431 and formed by bending downward (−Z side) by 90 degrees or more, and the back piece 434 is a plate-shaped member connected to the −Y side end of the bottom plate 431 and formed by bending upward by 90 degrees of more.

The bottom plate 431 has a plurality of holes 431a through which air circulating within the culture chamber 4b passes.

<Contact Relationship Among Shelf Support, Shelf Rest, Shelf Plate>

Figure 6:
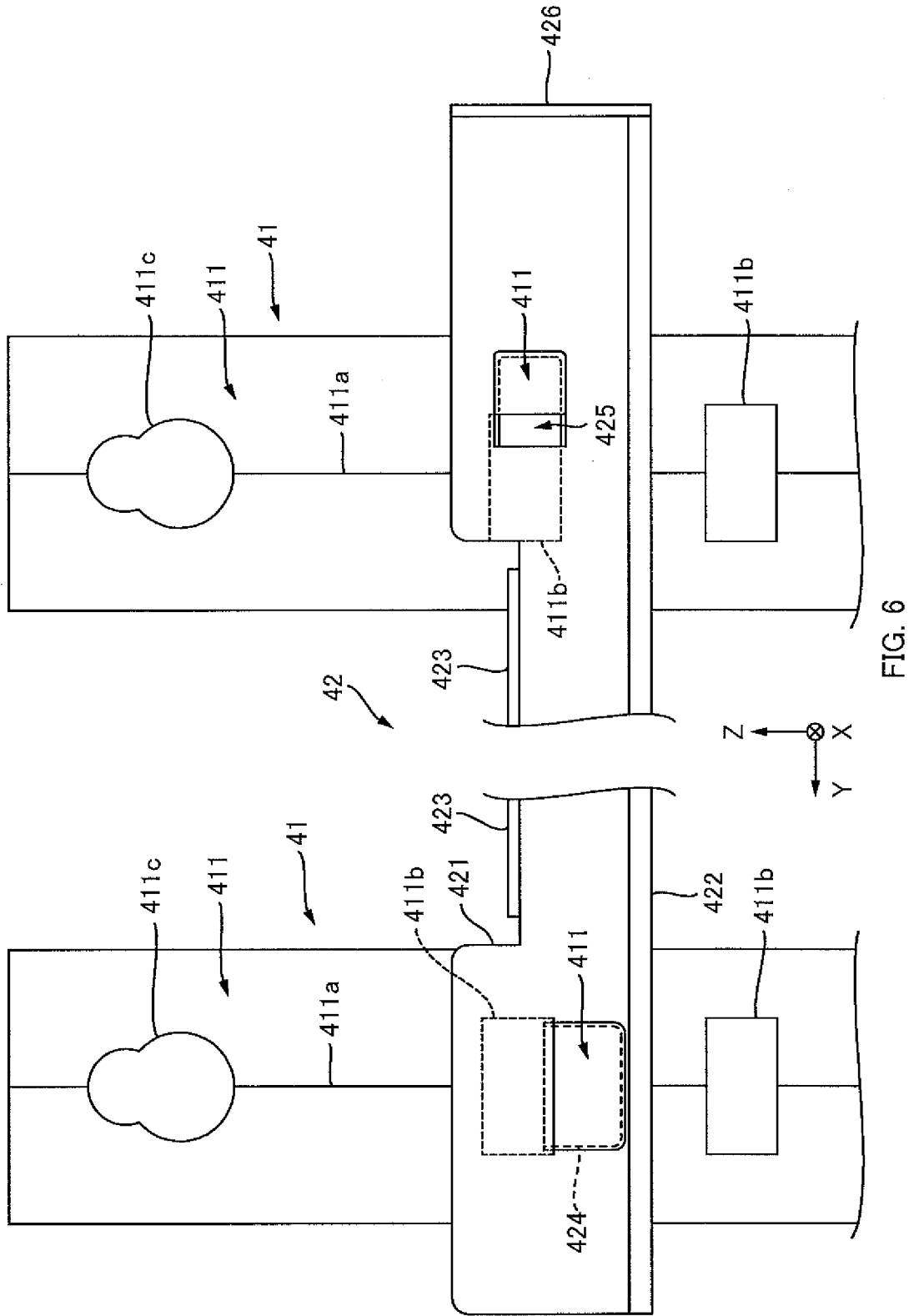
FIG. 6 is a diagram of a shelf support and a shelf rest in FIG. 1 viewed in the +X direction.

Referring to FIGS. 6 to 8, there will be described a contact relationship among the shelf support 41, the shelf rest 42, and the shelf plate 43 having the above configuration. FIG. 6 is a diagram of the shelf support 41 and the shelf rest 42 in FIG. 1 viewed in the +X direction. FIG. 7 is a diagram of the shelf support 41 and the shelf rest 42 in FIG. 1 viewed in the −Z direction. FIG. 8 is a sectional view illustrating cross sections of an inner face of the inner box 4, the shelf support 41 and the shelf rest 42 on an A-A' line in FIG. 7 and cross sections of the shelf plate 43 and the shelf rest 42' in the same cross section.

As exemplified in FIG. 6, the two shelf supports 41 are disposed in parallel in the horizontal direction (Y-axis direction) along the side face of the culture chamber 4b, and the shelf rest 42 is supported in the horizontal direction along the side face of the culture chamber 4b by the locking piece 424 and the locking piece 425 respectively locked into the pair of fitting-in holes 411b whose heights are equal.

As exemplified in FIG. 7, the faces of the pair of contact pieces 413 of the shelf support 41 on the side (+X side) closer to the side face of the culture chamber 4b and the inner face of the inner box 4 are in line contact with each other on a line Q in the longitudinal direction. As a result, a portion where the inner face of the inner box 4 and the shelf support 41 are in contact with each other is limited by the line Q, and therefore, the sterilizing gas can be distributed substantially uniformly over exposed faces in the vicinity around the line Q. Consequently, the exposed faces can be sufficiently sterilized, leading to improvement of the sterilization effect or the like of the culture apparatus 1.

Also, as exemplified in FIG. 7, the face of the shelf support 41 on the side (−X side) far from the side face of the culture chamber 4b in the bent plate 411 and the face of the vertical plate 421 of the shelf rest 42 on the side closer to the side face of the culture chamber 4b are in line contact with each other on a line P (that is, center line 411a) in the longitudinal direction. Also, the face of the bent plate 411 of the shelf support 41 on the side closer to the side face of the culture chamber 4b and both ends (±Y side end) in the fore-and-aft direction of the face of the locking piece 424 of the shelf rest 42 on the side far from the side face of the culture chamber 4b are in line contact with each other on a pair of lines R in the longitudinal direction. Also, the face of the bent plate 411 of the shelf support 41 on the side closer to the side face of the culture chamber 4b and the rear side end (−Y side end) of the face in the locking piece 425 of the shelf rest 42 on the side far from the side face of the culture chamber 4b are in line contact with each other on a line S in the longitudinal direction. As a result, since the portions in contact with each other between the shelf support 41 and the shelf rest 42 are limited to the lines P, R, and S, the sterilizing gas can be distributed substantially equally over the exposed faces in the vicinity around each of the lines P, R, and S. Thus, the exposed faces are sufficiently sterilized, leading to improvement of the sterilization effect of the culture apparatus 1 or the like. Also, the line contact on the lines 9, R, and S can be realized by such a configuration that the angle θ formed by the bent plate 411 is set at less than 180 degrees.

As exemplified in FIG. 8, the distal end of the rest piece 422 on the side (−X side) far from the side face of the culture chamber 4b when the shelf plate 43 is placed on the pair of shelf rests 42 and 42' and the +X side end on the lower face of the bottom plate 431 are in line contact with each other on a line T in the fore-and-aft direction (Y-axis direction).

Also, in mirror-symmetrical relation to the above with respect to a plane (not shown), serving as a boundary, at the center between the opposing side faces in the culture chamber 4b and in parallel with the side faces, a distal end on the side (+X side) far from the side face of the culture chamber 4b in the rest piece 422' when the shelf plate 43 is placed on the pair of shelf rests 42 and 42' and the −X side end on the lower face of the bottom plate 431 are in line with each other contact on a line T in the fore-and-aft direction. That is, since the pair of rest pieces 422 and 422' each extends obliquely more upward as it gets farther from the side faces of the culture chamber 4b, when the shelf plate 43 is placed on the pair of shelf rests 42 and 42', the shelf plate 43 is held horizontally with both side ends of the lower face thereof being, respectively, in line contact with the distal ends of the rest piece 422 and the rest piece 422'. As a result, since a portion where the shelf rest 42 and the shelf plate 43 are in contact with each other is limited to the portion of the line T, the sterilizing gas can be distributed substantially equally over the exposed faces in the vicinity around the line T. Thus, the exposed faces are sufficiently sterilized, leading to improvement of the sterilization effect of the culture apparatus 1 or the like. Also, the line contact on the line T can be realized by such a configuration that the angle θ' formed by the rest piece 422 relative to the vertical plate 421 is set at less than 90 degrees.

Though not shown, a position of the shelf plate 43 in the culture chamber 4b in the fore-and-aft direction (Y-axis direction) is determined when the rear side end (−Y side end) of the bottom plate 431 of the shelf plate 43 is brought into line contact with the stop piece 426 of the shelf rest 42. This line contact is caused by the fact that the back piece 434 of the shelf plate 43 is formed by bending upward (+Z side) by more than 90 degrees while being connected to the rear side end (−Y side end) of the bottom plate 431. This line contact also leads to improvement of the sterilization effect of the culture apparatus 1 or the like.

Other Embodiments

The above embodiments of the present invention are simply for facilitating the understanding of the present invention and are not in any way to be construed as limiting the present invention. The present invention may variously be changed or altered without departing from its spirit and encompass equivalents thereof.

In an embodiment as described above, the pair of rest pieces 422 and 422' each extends obliquely more upward as it gets farther from the side faces of the culture chamber 4b (angle θ' (<90 degrees) in FIG. 4A), however, this is not limitative. Even though the rest piece 422 is formed by bending in the orthogonal manner relative to the vertical plate 421, the distal end on the side far from the side face of the culture chamber 4b may be bent again upward (+Z side) so as to be in line contact with the lower face of the bottom plate 431 of the shelf plate 43 at the distal end.

In an embodiment as described above, the bent plate 411 is bent at the center line 411a serving as a line for bending, but this is not limitative. The bent plate 411 may simply form a curved face, for example, as long as it has such a shape as to become farthest from the side face of the culture chamber 4b substantially at the center of the bent plate 411 in a direction orthogonal to the longitudinal direction.

In an embodiment as described above, the contact between the rest piece 422 and the lower face of the bottom plate 431 on the line T is realized by the angle θ' (<90 degrees) of the rest piece 422 relative to the vertical plate 421, but this is not limitative. As exemplified in FIG. 9, even though a rest piece 922 may be orthogonal to a vertical plate 921 of a shelf rest 92, for example, a shelf plate 43' may have a bent projection 435' at the lower side (−Z side) thereof between a bottom plate 431' and a side piece 432', and the rest piece 922 and the bent projection 435' may be in line contact with each other on a line T'. FIG. 9 is a cross sectional view of the shelf rest 92 and the shelf plate 43' in cross section similar to that in FIG. 8.

In an embodiment as described above, the inner face of the inner box 4, the shelf support 41, the shelf rest 42, and the shelf plate 43 are in line contact with each other on the lines P, Q, R, S, and T, however, this is not limitative. For example, as exemplified in FIGS. 10 and 11, they may be in point contact. FIG. 10 is a view of the inner face of the inner box 4, a shelf support 81, and a shelf rest 82 when viewed from the direction similar to that in the case of FIG. 7, and FIG. 11 is a cross sectional view of the inner face of the inner box 4, the shelf support 81, the shelf rest 82, and the shelf plate 43 in a section similar to that in FIG. 8.

As exemplified in FIG. 10, projections 813a substantially in the semispherical shape on faces (in parallel with the YZ face) on the side (+X side) closer to the side face of the culture chamber 4b in a pair of contact pieces 813 of the shelf support 81 and the inner face of the inner box 4 are in point contact at points Q'. Also, projections 811a substantially in the semispherical shape on a face (in parallel with the YZ face) on the side (−X side) far from the side face of the culture chamber 4b in a flat plate 811 of the shelf support 81 and a face on the +X side of a vertical plate 821 of the shelf rest 82 are in point contact at points P'. Also, projections 811b substantially in the semispherical shape on a face (in parallel with the YZ face) on the side (+X side) closer to the side face of the culture chamber 4b in the flat plate 811 of the shelf support 81 and the ±Y side ends on a face on the side far from the side face of the culture chamber 4b in a locking piece 824 of the shelf rest 82 are in point contact at points R'.

As exemplified in FIG. 11, a projection 822a substantially in the semispherical shape on an upper face (in parallel with the XY face) of a rest piece 822 of the shelf rest 82 and the +X side end on the lower face of the bottom plate 431 of the shelf plate 43 are in point contact at a point T".

The projections 811a, 811b, 813a, and 822a exemplified in FIGS. 10 and 11 may be formed by pressing a plate member, for example, from a face on the side opposite to the side on which the projections are to be formed with a tool in a similar shape to the projections to such a degree that the projections are formed.

Second Embodiment

In a culture apparatus, temperature and gas concentration of carbon dioxide ($CO_2$), oxygen ($O_2$) and the like within the culture chamber is maintained constant, and the inside of the culture chamber is kept in an aseptic state, so that culture such as a cell, and a microorganism is cultured. In such a culture apparatus, the gas concentration in the culture chamber is detected by a sensor, and gas supply into the culture chamber is controlled so that the gas concentration is maintained constant. In general, when the gas concentration in the culture chamber is detected, atmospheric gas (hereinafter referred to simply as gas) consisting principally of air in the culture chamber is sucked into piping connected to the outside of the culture apparatus, concentration of the sucked gas is detected, and then, the gas is returned into the culture chamber. In order to suck the gas from the culture chamber into the piping and to return it into the culture chamber again, a suction device such as a pump and a fan is used (See Japanese Patent Laid-Open Publication No. 2007-259715, for example).

By using the suction device as such, the gas in the culture chamber can be forcedly led to the piping and at the same time, a flow velocity of the gas in the piping can be controlled to a velocity suitable for detection by the sensor. However, since the suction device is required, a cost and power consumption are increased by that portion, as well as if the suction device fails to operate properly, the gas concentration cannot be detected accurately, and it becomes difficult to maintain the gas concentration in the culture chamber constant.

Thus, an embodiment of the present invention has an object to detect concentration of gas in a culture chamber without using a suction device.

FIG. 12 is a cross sectional view of a culture apparatus, which is a second embodiment of the present invention, viewed from a side face. A culture apparatus 10A includes an outer box 12A and an inner box 14A. The outer box 12A includes an insulating material 16A inside and the inner box 14A further inside through a space 18A. A transparent inner door 20A for closing an opening portion of the inner box 14A so as to be openable/closable is provided on the front face of the inner box 14A, an outer door 22A is further provided on the outside, and the outer door 22A includes an insulating material 24A inside.

A space in the inner box 14A sealed by the inner door 20A is a culture chamber 26A. In the culture chamber 26A, a shelf 28A having a large number of vents is provided, and a case containing culture is placed on the shelf 28A in a state where the outer door 22A and the inner door 20A are opened. Then, the culture placed on the shelf 28A is cultured in the culture chamber 26A in a state where the outer door 22A and the inner door 20A are closed. During the culturing, by opening only the outer door 22A, the inside of the culture chamber 26A can be observed in a state where the inner door 20A is kept closed.

On a back face 30A in the inner box 14A, a fan (sirocco fan) 32A for circulating the gas in the culture chamber 26A is provided. A motor 33A for driving the fan 32A is provided in the space 18A. Also, in the culture chamber 26A, a wall plate 34A is provided so as to cover a part of the fan 32A and the back face 30A. On the wall plate 34A, a suction port 36A is provided in the vicinity of a spot covering the fan 32A, and a duct 38A (air passage) is formed through which the gas sucked from the suction port 36A flows. That is, the gas in the culture chamber 26A is sucked from the suction port 36A at the upper part of the back face 30A by rotation of the fan 32A, flows from the upper part to the lower part in the duct 38A, and returns to the culture chamber 26A from the lower part of the back face 30A. The gas discharged from the lower part of the duct 38A flows from a bottom face 40A toward a top face 42A of the inner box 14A through the vents in the shelf 28A and is sucked from the suction port 36A again. As a result, the gas in the culture chamber 26A is circulated.

An injection port 48A for supplying $CO_2$ gas into the culture chamber 26A is provided penetrating from a back face 44A of the outer box 12A to the duct 38A in the inner box 14A. Moreover, a temperature sensor 50A is provided penetrating from the back face 44A of the outer box 12A to the duct 38A in the inner box 14A. A temperature inside the culture chamber 26A is detected by the temperature sensor 50A, and a heater for heating the inside of the culture chamber 26A is controlled so that temperature in the culture chamber 26A becomes suitable for culturing.

In a region covered by the wall plate 34A in the back face 30A of the inner box 14A, there are provided a through hole 52A (first through hole) and a through hole 54A (second through hole) penetrating from the back face 30A of the inner box 14A to the back face 44A of the outer box 12A. Into the through holes 52A and 54A, a tube 56A (connecting pipe) having flexibility is inserted from the back face 44A side of the outer box 12A so that the outer periphery of the tube 56A is in close contact with the inner peripheries of the through holes 52A and 54A. That is, the gas in the culture chamber 26A is in such a state as to be capable of flowing through the tube 56A. At a part of the tube 56A projecting to the outside of the outer box 12A, there is provided a concentration sensor 58A for detecting concentration of the $CO_2$ gas flowing through the tube 56A. As the concentration sensor 58A, an infrared type can be used, for example. In the case of the infrared type, by heating a ceramic heater, an infrared ray, in the vicinity of 4.3 μm to be absorbed by the $CO_2$ gas is generated to be applied to the gas flowing through the tube 56A, and a light receiving element detects a light amount of the infrared ray having passed through the gas so that the concentration of the $CO_2$ gas can be measured. As the concentration sensor 58A, there can be also used those other than the infrared type such as heat conduction type.

Also, a portion of the tube 56A projecting to the outside of the outer box 12A is in a closed space 61A covered by a heater 60A (heating device). The inside of the culture chamber 26A is maintained at a temperature of the order of 37° C. and humidity of the order of 95%, for example, however, if the temperature of the closed space 61A is lower than that, there is a fear that condensation occurs in the tube 56A. Thus, the inside of the closed space 61A including the portion of the tube 56A projecting to the outside of the outer box 12A is heated by the heater 60A to be maintained at a temperature on the order of 45° C., for example. Also, by keeping the temperature inside the closed space 61A constant, such an effect is realized that sensitivity of the concentration sensor 58A can be made constant, as well.

Other than the above, in the culture apparatus 10A, a sensor for detecting humidity in the culture chamber 26A is provided, and by controlling heating of a water plate placed on the bottom face 40A of the inner box, humidity in the culture chamber 26A is maintained constant.

FIG. 13 is a diagram illustrating a part of the back face 44A of the outer box 12A in the culture apparatus 10A. On the back face 44A of the outer box 12A, the tube 56A inserted into the through holes 52A and 54A is projected. The concentration sensor 58A is disposed so as to be capable of detecting the $CO_2$ concentration in the tube 56A. The tube 56A connecting between the through holes 52A and 54A may be a single tube penetrating through the concentration sensor 58A or may be made up of two tubes, that is, a tube connecting between the through hole 52A and the concentration sensor 58A and a tube connecting between the through hole 54A and the concentration sensor 58A. A gas cylinder filled with $CO_2$ gas is connected to a connection port 66A of a pipe 64A. The pipe 64A is connected to the injection port 48A of the culture chamber 26A, and the $CO_2$ gas supplied to the connection port 66A is supplied to the culture chamber 26A through a filter 68A and a valve 70A. A control device 72A controls temperature and gas concentration of the culture apparatus 10A and includes a microcomputer or the like. For example, the control device 72A adjusts supply of $CO_2$ gas into the culture chamber 26A by controlling opening/closing of the valve 70A on the basis of a detection result of the concentration sensor 58A.

FIG. 14 is a front view of the culture apparatus 10A when the outer door 22A and the inner door 20A are in an opened state. As mentioned above, when the fan 32A is rotated, the gas in the culture chamber 26A is sucked from the suction port 36A provided in the wall plate 34A. Then, the sucked gas is discharged from the entire outer periphery of the fan 32A, however, being surrounded by the wall plate 34A above and on the right and left sides, the gas in the duct 38A flows from the upper part to the lower part while being agitated in the duct 38A, is discharged from the lower part of the duct 38A into the culture chamber 26A, and is circulated. Here, the through hole 54A is provided on the downstream position from the through hole 52A in the flow direction of the gas in the duct 38A. Since the flow velocity of the gas flowing through the duct 38A is reduced as the gas goes away from the fan 32A, the flow velocity in the vicinity of the through hole 52A becomes slightly faster than the flow velocity in the vicinity of the through hole 54A. A gas atmospheric pressure decreases as the flow velocity increases, and thus, the atmospheric pressure in the vicinity of the through hole 52A is lower than that in the vicinity of the through hole 54A. Due to this difference in atmospheric pressure, the gas in the vicinity of the through hole 54A flows in a direction of the through hole 52A through the tube 56A. That is, in the culture apparatus 10A, the gas in the culture chamber 26A can be allowed to flow through the tube 56A without using a suction device such as a pump, so that the concentration of the $CO_2$ gas can be detected.

Also, in the duct 38A, the injection port 48A is disposed on the upstream position in the flowing direction of the gas in the duct 38A from the through holes 52A and 54A. Also, the injection port 48A is disposed at a position displaced to the left side, when viewed toward the back face 30A, from a position connecting between the fan 32A and the through holes 52A and 54A so that the $CO_2$ gas is injected to the left side when viewed toward the back face 30A. That is, while the $CO_2$ gas is injected from the injection port 48A in a direction different from the flowing direction of the gas circulating in the culture chamber 26A. The $CO_2$ gas injected from the injection port 48A is being mixed with gas sucked from the suction port 36A by an air current caused by the fan 32A, the $CO_2$ gas flows from the upper part to the lower part in the duct 38A to be supplied to the culture chamber 26A. Since the injection port 48A is disposed in a position close to the fan 32A, the $CO_2$ gas injected from the injection port 48A can easily be agitated, and response at a time when the concentration of the $CO_2$ gas in the culture chamber 26A is adjusted can be improved. Also, since the direction in which the $CO_2$ gas is injected from the injection port 48A is different from the flowing direction of the gas in the duct 38A, the $CO_2$ gas with high concentration injected from the injection port 48A is prevented from directly flowing into the vicinity of the through holes 52A and 54A, and thus, the detection accuracy of the concentration of the $CO_2$ gas in the in the culture chamber 26A can be improved.

FIGS. 15 and 16 are experimental results illustrating examples of $CO_2$ gas concentration when the outer door 22A and the inner door 20A are opened/closed. A graph shown by a solid line in FIG. 15 shows change in the $CO_2$ gas concentration in a case where the outer door 22A and the inner door 20A is opened and kept open for 30 seconds and then, closed, from a state in which the $CO_2$ gas concentration in the culture chamber 26A is maintained at approximately 5%. Also, a graph shown by a solid line in FIG. 16 shows a case where a time period during which the outer door 22A and the inner door 20A is open is set to 60 seconds. Graphs shown by broken lines in FIGS. 15 and 16 show change in the $CO_2$ gas concentration in a case with the same configuration as that of the culture apparatus 10A except that there is provided a pump for sucking the gas in the culture chamber 26A from the through hole 52A and returning it to the through hole 54A.

As shown by the graphs in FIGS. 15 and 16, when the outer door 22A and the inner door 20A are opened, the $CO_2$ gas concentration in the culture chamber 26A is reduced, and thus, when the outer door 22A and the inner door 20A are closed, the control device 72A controls opening/closing of the valve 70A on the basis of a detected value of the concentration sensor 58A so that the $CO_2$ gas concentration in the culture chamber 26A returns to approximately 5%. As known from these graphs, a time period from a time when the outer door 22A and the inner door 20A are closed to a time when the $CO_2$ gas concentration returns to approximately 5% is substantially equal between the case in the culture apparatus 10A of an embodiment of the present invention having the configuration without a pump and the case in an apparatus having a configuration with a pump. From these experimental results, it can be understood that the gas flows through the tube 56A at a speed suitable for detection by the concentration sensor 58A so that the $CO_2$ gas concentration can be detected accurately, although the culture apparatus 10A does not include a suction device such as a pump.

According to an embodiment of the present invention, the duct 38A is provided on the back face 30A side of the inner box 14A, however, it may be provided on the side face side. Also, the fan 32A may be disposed on the top face 42A of the inner box 14A, and the through holes 52A and 54A may be provided on the back face 30A or the side face of the inner box 14A. Moreover, the through holes 52A and 54A may be provided on the top face of the inner box 14A. Also, in the culture apparatus 10A, the through holes 52A and 54A are disposed on the same straight line when viewed from the fan 32A, however, they do not have to be disposed on the same straight line as long as they are disposed in the positions between which the flow velocities are different. Moreover, the through holes 52A and 54A may be provided not on the same plane but on different planes in the inner box 14A. Also, the tube connected to the through holes 52A and 54A may be disposed in the space 18A between the outer box 12A and the inner box 14A without projecting to the outside of the outer box 12A. Also, if it is possible that the gas in the culture chamber 26A is circulated, and that the flow velocities around the through holes 52A and 54A are different, the wall plate 34A does not have to be included in the configuration.

Also, as a configuration in which culture is placed on the shelf 28A, the shelf support 41, the shelf rests 42 and 42', and the shelf plate 43 in a first embodiment of the present invention, may be employed so that the inside of the inner box 14A can be sufficiently sterilized by sterilizing gas.

Third Embodiment

<Configuration of Culture Apparatus>

Figure 18:
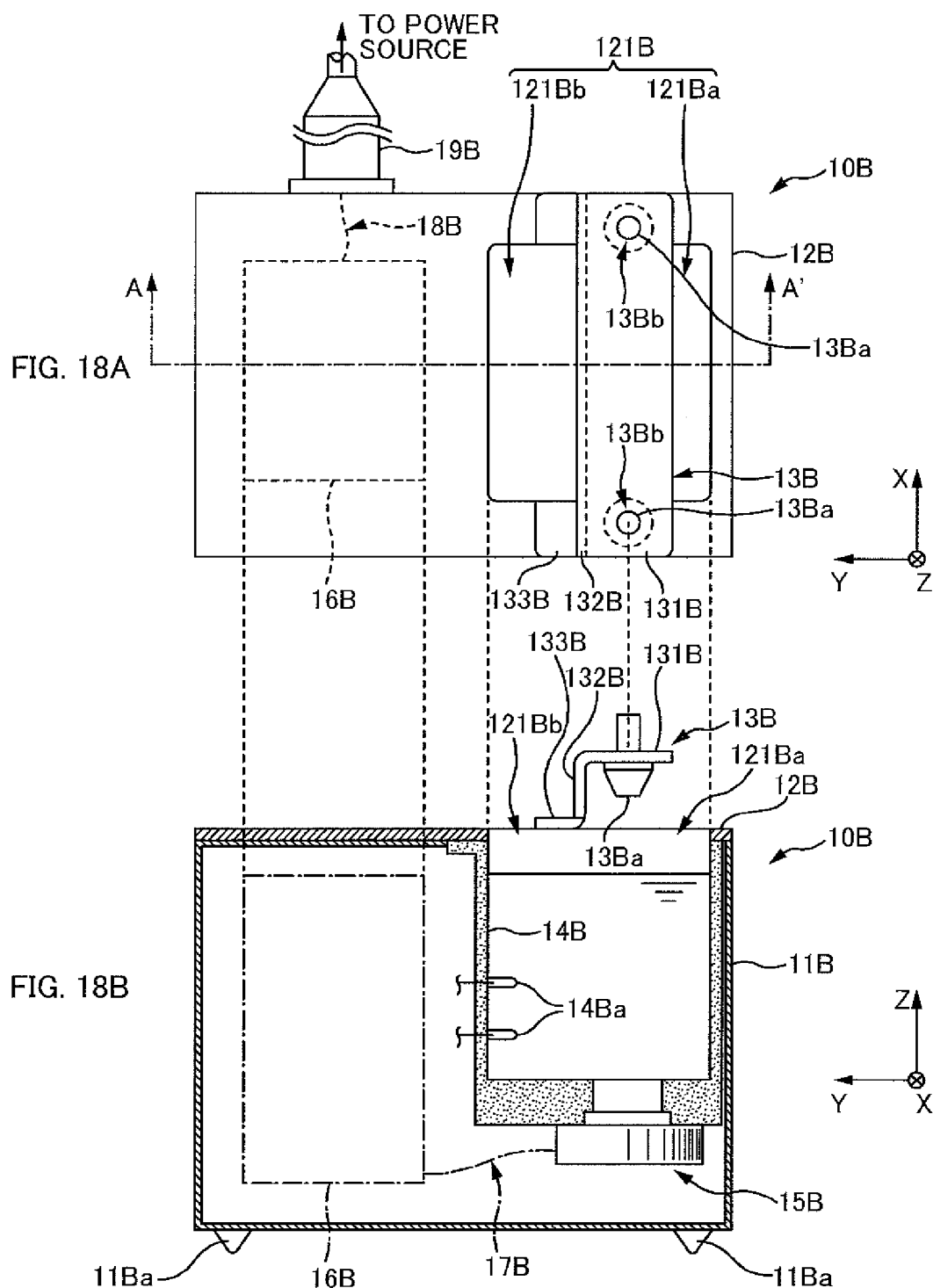

Referring to FIGS. 17 to 19, there will be described a configuration example of a culture apparatus 1B of a third embodiment of the present invention. FIG. 17 is aside sectional view of an example of the culture apparatus 1B according to a third embodiment of the present invention. FIG. 18A is a plan view of an example of a gas generator 10B according to a third embodiment of the present invention. FIG. 18B is a partial sectional view of the gas generator 10B on an A-A' line in FIG. 18A. FIG. 19 is an enlarged view of the gas generator 10B in FIG. 17 and in the vicinity thereof.

As exemplified in FIG. 17, the culture apparatus 1B includes a duct 43B, a fan 5Ba, and the gas generator 10B. In the culture apparatus 1B, culture such as a cell, a microorganism, and the like is cultured within a culture chamber 4Bb of an inner box 4B.

The inner box 4B is a substantially solid rectangular box made of stainless steel, for example, and includes the culture chamber 45b therein. For the inner box 4B, an inner door 4Ba is provided openable/closable through a predetermined hinge (not shown). This inner door 4Ba is in a flat-plate shape made of tempered glass, for example, and when an opening on the front side (+Y side) of the inner box 4B is closed through predetermined packing (not shown), the inside of the inner box 4B is made air tight against the outside. The culture chamber 4Bb exemplified in FIG. 17 is partitioned in the vertical direction (Z-axis direction) by a plurality of shelves 42B made of stainless steel, for example, on which culture is placed. This shelf 42B has a plurality of holes (not shown) penetrating the shelf in the vertical direction, and is supported by a shelf rest 41B which is made of stainless steel, for example, and is provided in a pair on an inner face on the ±X side of the inner box 4B.

The duct 43B is made up of a wall on the rear side (−Y side) of the inner box 4B and a wall plate 5B made of stainless steel, between which an air passage is formed. The wall plate 53 exemplified in FIG. 17 includes an upper end portion 51B in an upper part, a center portion 52B, and a lower end portion 53B in a lower part. The upper end portion 51B is in such a shape as to surround blades of the fan 5Ba with a predetermined space and includes a suction port 51Ba. The center portion 52B is in a U-shape in cross section in the horizontal direction (X, Y axis directions), and includes a portion in contact with the inner face on the rear side of the inner box 4B on the ±X side and a portion opposing the inner face with a predetermined space. The lower end portion 53B is a short piece formed by bending a flat plate portion at the lower end in the vertical direction to be extended in the horizontal direction on the +Y side, and has a predetermined space between the piece and the bottom face of the inner box 43 in the vertical direction. At a lower part (−Z side) of the duct 43B exemplified in FIG. 17 and on the inner face on the rear side of the inner box 4B, there is mounted an ultraviolet lamp 53b for applying an ultraviolet ray to the air passing through the duct 43B, for example.

The fan 5Ba is a sirocco fan provided at an upper part (+Z side) of the duct 43B and on the inner face on the rear side of the inner box 4B with a rotation axis in the Y-axis direction, for example. This fan 53a is rotated in a predetermined direction by a predetermined power source (not shown) such as a motor, and thus, a circulation path is made up in which the air in the culture chamber flows into the duct 43B through the suction port 51Ba, flows from the upper part to the lower part in the duct 43B, and returns into the culture chamber through the opening at the lower part of the duct 43B.

The above-mentioned inner box 4B is housed in an outer box 2B substantially in a solid rectangular shape which is made of stainless steel, for example. The outer box 2B is a box made of metal and having a shape substantially similar to that of the inner box 4B, for example, and includes an insulating material (not shown) inside for thermal insulation. An air jacket 6B is formed between the outer box 2B and the inner box 4B as an air circulation path, for example, for further thermal insulation, and a heater (not shown) for adjusting temperature inside the culture chamber 4Bb is mounted on the air jacket 6B.

Also, on the outer box 2B, there is provided an outer door capable of opening/closing the opening through a predetermined hinge (not shown). The outer door 3B includes: a door main body 31B made of metal including an insulating material (not shown) for thermal insulation, a heater (not shown) for adjusting the temperature in the culture chamber 4Bb and the like in the inside of the door main body and packing 33B mounted on a projection portion 31Ba opposing the opening of the outer box 2B in the door main body 31B. This outer door 3B further includes, for example, a control panel 32B on the front side of the door main body 31B. This control panel 32B includes a key for setting a temperature, concentration of carbon dioxide and the like in the culture chamber 4Bb, a display for displaying their current values and the like and also has a control portion (not shown) for controlling a sensor or the like for detecting these temperature, concentration and the like, for example.

Moreover, on the outer face on the rear side of the outer box 2B, there are provided, for example, a sensor box 7B including a sensor (not shown) for detecting a temperature in the culture chamber 4Bb, a sensor (not shown) for detecting concentration of carbon dioxide, a heater (not shown) and the like. These sensors are mounted from outside the outer box 2B through a hole (not shown) drilled from the outer face on the rear side of the outer box 2B to the inner face on the rear side of the inner box 4B. Also, these sensors are electrically connected to the above-mentioned control portion of the control panel 32B through a predetermined wiring (not shown). The control portion controls operations of the heater, the fan 53a, the ultrasonic vibrator 15B of the gas generator 10B and the like. Also, the outer face on the rear side of the outer box 2B and the sensor box 7B are covered by a cover 21B including an insulating material (not shown) inside.

<Gas Generator>

As exemplified in FIGS. 18A and 18B, the gas generator 10B according to an embodiment of the present invention includes a tank 14B in which hydrogen peroxide solution is stored, the ultrasonic vibrator 15B for generating gas (hydrogen peroxide) by atomizing hydrogen peroxide solution, and an opening 121B of the tank 14B, and the opening 121B is split into an admission port 121Ba for admitting air into the tank 14B and a discharge port 121Bb for discharging the air with the hydrogen peroxide gas from the tank 14B into the culture chamber. A suppressing plate 13B, a locking pin 13Ba, and the ultrasonic vibrator 15B exemplified in FIGS. 18B and 19 are shown not in a section on A-A' line but in a side face viewed in the X-axis direction for convenience of the following explanation.

In the exemplification of the same figures, a top plate 12B with an opening substantially in a rectangular shape made of metal, for example, is mounted on housing 11B with an opening substantially in a solid rectangular shape made of metal, for example, while supporting the tank 14B with the ultrasonic vibrator 15B mounted at the lower part (−Z side) thereof in such a manner that the opening 121B is directed upward (+Z side). On a side face on the +X side of the housing 11B with the opening, there is mounted a wiring connector 19B for power supply from a power source, not shown.

A space formed by being sectionalized by the top plate 12B with the opening on which the tank 14B is mounted and the housing 11B with the opening is air tight against the outside. In this air-tight space, there are housed the ultrasonic vibrator 15B, a control board 16B for controlling an operation of the ultrasonic vibrator 15B, wiring 17B for electrically connecting between the ultrasonic vibrator 15B and the control board 16B, and wiring 18B for electrically connecting between the control board 16B and the wiring connector 19B.

As exemplified in FIGS. 18A, 18B, and 19, the suppressing plate 13B is provided upright substantially at the center part in the Y-axis direction around the opening 121B of the top plate 12B with the opening, by which the opening 121B is divided into the admission port 121Ba and the discharge port 121Bb. This suppressing plate 13B has a function to suppress inflow of the air discharged from the duct 43B into the discharge port 121Bb and also has a function to fix the gas generator 10B at a suitable position on the wall plate 5B so that the air can effectively flow into the admission port 121Ba.

Specifically, the suppressing plate 13B is a plate material made of metal integrally including a horizontal portion 131B substantially in a rectangular shape, a vertical portion 132B orthogonal to the horizontal portion 131B along the X-axis direction, and a pair of horizontal pieces 133B orthogonal to both ends of the vertical portion 132B along the X-axis direction and parallel with the horizontal portion 131B. The pair of horizontal pieces 133B is fixed around the opening 121B so that the vertical portion 1323 is positioned substantially at the center part in the Y-axis direction in the opening 121B. Also, in through holes 13Bb on the ±X sides of the horizontal portion 131B, there are provided the locking pins 13Ba in a pair substantially in a cone shape toward the lower part (−Z side) and made of metal, for example.

As exemplified in FIG. 19, the lower end portion 53B of the wall plate 53 has a pair of locking holes 53Ba along the X-axis direction. The pair of locking holes 53Ba is located on both sides in the X-axis direction in the lower end portion 53B of the wall plate 5B, for example. Also, a distance between centers of the two locking holes 53Ba is set equally to a distance between centers of the two locking pins 13Ba exemplified in FIG. 18A. Moreover, as exemplified in FIG. 19, the maximum diameter of the cone shaped portion of the locking pin 13Ba is set slightly smaller than a diameter of the locking hole 53Ba.

From the above configuration, as exemplified in FIG. 19, if the gas generator 10B is attached to the duct 43B by fitting and inserting the pair of locking pins 13Ba of the suppressing plate 13B into the pair of locking holes 53Ba of the lower end portion 53B of the wall plate 5B, respectively, the lower end portion 53B of the wall plate 5B and the horizontal portion 131B of the suppressing plate 13B are in such a relationship that they are overlapped with each other in the Y-axis direction and the horizontal portion 131B is positioned substantially at the center of the lower end portion 53B in the X-axis direction. That is, with regard to the tank 14B of the gas generator 10B, the admission port 121Ba is located on the duct 43B side, while the discharge port 121Bb is located on the shelf 42B side. On the other hand, the gas generator 10B can be dismounted from the duct 43B by slightly lifting the suppressing plate 13B up and removing the pair of locking pins 13Ba from the pair of locking holes 53Ba, respectively.

As exemplified in FIG. 19, at four corners on the outer face substantially in the rectangular shape on the lower side of the housing 11B with the opening, four legs 11Ba each substantially in a cone shape toward the lower part, for example, are provided so that they are each in point contact with the bottom face of the culture chamber 4Bb.

Also, the tank 14B is provided with a sensor 14Ba for detecting a water level of hydrogen peroxide solution. The sensor 14Ba has a pair of metal pins, for example, and the pair of metal pins is provided so as to project inward from the inner face of the tank 14B with a predetermined space in the Z-axis direction. The above-mentioned control portion measures a resistance value between the metal pins in a pair, for example, and if it determines that the water level of the hydrogen peroxide solution in the tank 14B has not reached a predetermined value on the basis of a measurement result, the control portion prohibits the ultrasonic vibrator 15B from being operated. As a result, the ultrasonic vibrator 15B can be prevented from being erroneously operated when the tank 14B is empty, for example. Thus, there can be prevented deterioration or failure caused by heat of the ultrasonic vibrator 15B, which is overheated by operation in a state where there is no hydrogen peroxide solution.

Moreover, when the gas generator 10B is arranged in the culture chamber 4Bb, a male connector (not shown), for example, of wiring (not shown) from the wiring connector 19B of the gas generator 10B is connected to a female connector (not shown), for example, of wiring (not shown) in the culture chamber 4Bb connected to the above-mentioned power source so that they are electrically connected. The pair of connectors is resistant to water and corrosion. On the other hand, when the gas generator 10B is demounted from the culture chamber 4Bb, it is only necessary to disconnect the male connector and the female connector, which have been connected.

<Operation of Culture Apparatus>

Referring to FIGS. 20 and 21, there will be described an operation example of the culture apparatus 1B provided with the above-mentioned configuration. FIG. 20 is a schematic diagram illustrating an example of an air passage in the culture chamber 4Bb during culturing of the culture apparatus 1B in FIG. 17. FIG. 21 is a schematic diagram illustrating an example of an air passage in the culture chamber 4Bb during a sterilizing operation of the culture apparatus 1B in FIG. 17.

As exemplified in FIG. 20, a humidification tray 44B made of stainless steel, for example, filled with water for humidification is arranged on the bottom face in the culture chamber 4Bb so that a part thereof is located immediately below the duct 43B, during culturing. Also, the entire humidification tray 44B is covered by a cover 45B made of stainless steel, for example, having a hole 45Ba on the front thereof.

As exemplified by framed arrows in the same figure, by rotation of the fan 5Ba, the air on the upper shelf 42B side in the culture chamber 4Bb flows into the duct 43B through the suction port 51Ba, flows from the upper part to the lower part in the duct 43B and then, flows on the water face of the water for humidification to the front, and the humidified air passes through the hole 45Ba of the cover 45B and forms a rising air current surrounding the plurality of shelves 42B. The air having risen to the upper part of the culture chamber 4Bb flows into the duct 43B again through the suction port 51Ba. By such circulation of the air, the inside of the culture chamber 4Bb is maintained at substantially uniform temperature, humidity and carbon dioxide concentration, for example.

As exemplified in FIG. 21, during sterilizing operation, the gas generator 10B with hydrogen peroxide solution stored in the tank 14B is arranged on the bottom face in the culture chamber 4Bb so as to take a relative position with respect to the duct 43B shown in FIG. 21.

As exemplified by the framed arrows in the same figure, by rotation of the fan 5Ba, the air on the upper shelf 42B side in the culture chamber 4Bb flows into the duct 43B through the suction port 51Ba, and flows from the upper part to the lower part in the duct 43B, and then, at least a part thereof flows into the tank 14B through the admission port 121Ba of the gas generator 10B, changes the direction of the air current upward on the water face of the hydrogen peroxide solution, and is discharged from the discharge portion 121Bb of the gas generator 10B with the hydrogen peroxide atomized by the operation of the ultrasonic vibrator 15B, to form a rising air current surrounding the plurality of shelves 42B. Then, the air having risen to the upper part in the culture chamber 4Bb flows into the duct 43B again through the suction port 51Ba.

According to the culture apparatus 1B as described above, during the sterilizing operation, uniformity of the hydrogen peroxide gas in the culture chamber 4Bb can be improved utilizing the fan 5Ba and the duct 43B (See FIG. 20) which is used during culturing. That is, since the hydrogen peroxide gas is discharged to the upper part in the culture chamber 4Bb by a circulated air current formed by the fan 5Ba and the duct 43B (See FIG. 21), uniformity of the hydrogen peroxide gas is improved, which has greater specific gravity than that of air and is likely to remain at the lower part of the culture chamber 4Bb. This leads to improvement of the sterilization effect of the culture apparatus 1B. Moreover, since the gas generator 10B does not have to be individually provided with an electric power means such as a fan for such uniformity, there is no possibility of failures such as corrosion of the means caused by the hydrogen peroxide gas or electric leakage caused by humidity. As a result, stability of the sterilization effect is improved in the culture apparatus 1B.

Furthermore, according to the culture apparatus 13, since the admission port 121Ba and the discharge port 121Bb of the gas generator 10B are formed by being divided by the suppressing plate 13B, the air to be discharged from the discharge port 121Bb is not disturbed by the air flowing downward through the duct 43B, for example, but is effectively discharged upward in the culture chamber 4Bb. Also, by the above-mentioned engagement between the suppressing plate 13B and the lower end portion 53B, the gas generator 10B can be arranged in a suitable position with respect to the duct 43B so that the air from the duct 43B is effectively admitted into the tank 14B. As a result, uniformity of the hydrogen peroxide gas in the culture chamber 4Bb is further improved, and the sterilization effect of the culture apparatus 1B is also further improved.

In addition, according to the culture apparatus 1B, since each of the plurality of legs 11Ba of the gas generator 10B are in point contact with the bottom face of the culture chamber 4Bb, substantially the entire surface of the bottom face can be exposed to the hydrogen peroxide gas. This leads to improvement of the sterilization effect of the culture apparatus 1B.

Other Embodiments

In an embodiment as mentioned above, the fan 5Ba is provided on the inner face on the rear side of the inner box 4B, however, this is not limitative. The fan 5Ba may be provided on the inner side on the ±X side of the inner box 4B, for example (See FIG. 17) or may be provided on the top face of the inner box 4B, for example.

In an embodiment as mentioned above, the duct 43B is made up of the wall on the rear side of the inner box 4B and the wall plate 5B, however, this is not limitative. The duct 43B may be of any configuration or may be provided at any location in the culture chamber 4Bb as long as the duct does not occupy too much space in the culture chamber 4Bb, does not obstruct culturing of the culture, guides the air from the fan 5Ba from the upper part to the lower part of the culture chamber 4Bb, and is easy to be sterilized.

In an embodiment as mentioned above, the engagement between the duct 43B and the suppressing plate 13B of the gas generator 10B is through the pair of locking holes 53Ba in the lower end portion 53B of the wall plate 5B and the pair of locking pins 13Ba, however, this is not limitative. A means for attaching and detaching between the duct 43B and the suppressing plate 13B may be of any configuration as long as the mean has such a simple shape as to be capable of being easily sterilized, for example.

Also, as a configuration for placing the culture on the shelf 42B, the shelf support 41, the shelf rests 42 and 42', and the shelf plate 43 of a first embodiment of the present invention may be employed so that the inside of the inner box 4B is sufficiently sterilized by the sterilizing gas.

What is claimed is:

1. A culture apparatus comprising:
   a culture chamber including a shelf on which culture is placed;
   a fan configured to circulate air inside the culture chamber in a predetermined direction in the culture chamber;
   a duct configured to guide air circulating inside the culture chamber along a wall face inside the culture chamber from an upper part to a lower part of the culture chamber; and
   a gas generator including a tank in which a hydrogen peroxide solution is stored and an ultrasonic vibrator configured to atomize the hydrogen peroxide solution to generate a hydrogen peroxide gas for sterilizing the inside of the culture chamber,
   the tank including an admission port configured to admit air into the tank and a discharge port configured to discharge the hydrogen peroxide gas into the culture chamber with the air admitted into the tank,
   the duct including a wall plate and an air passage formed between the wall face and the wall plate,
   the gas generator including a fixing plate configured to fix the gas generator onto the wall plate, the fixing plate being detachably engaged with the wall plate, and
   the admission port being located on the duct side and the discharge port being located on the shelf side by engaging the fixing plate with the locking portion wall plate.

2. The culture apparatus according to claim 1, wherein the gas generator includes a plurality of legs configured to be in point contact with a bottom face of the culture chamber.

* * * * *